Figure 1A:
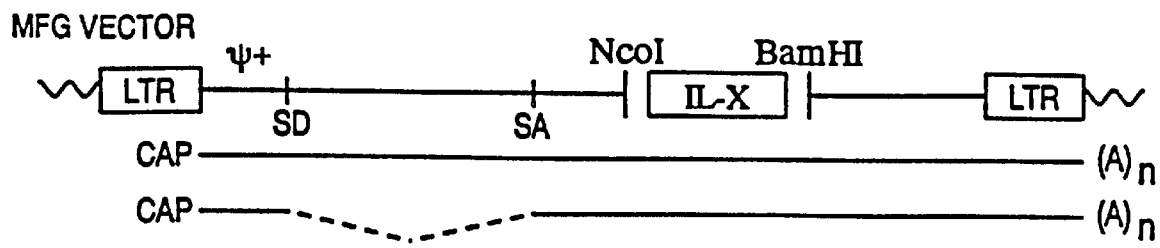

US005904920A

United States Patent [19]
Dranoff et al.

[11] Patent Number: 5,904,920
[45] Date of Patent: *May 18, 1999

[54] REGULATION OF SYSTEMIC IMMUNE RESPONSES UTILIZING CYTOKINES AND ANTIGENS

[75] Inventors: Glenn Dranoff, Lexington; Richard C. Mulligan, Lincoln, both of Mass.; Drew Pardoll, Baltimore, Md.

[73] Assignees: Whitehead Institute for Biomedical Research, Cambridge, Mass.; Johns Hopkins University School of Medicine, Baltimore, Md.

[*] Notice: This patent is subject to a terminal disclaimer.

[21] Appl. No.: 08/486,854

[22] Filed: Jun. 7, 1995

Related U.S. Application Data

[63] Continuation-in-part of application No. 08/265,554, Jun. 23, 1994, Pat. No. 5,637,483, which is a continuation of application No. 07/956,621, Oct. 5, 1992, abandoned, which is a continuation-in-part of application No. 07/771,194, Oct. 4, 1991, abandoned.

[51] Int. Cl.$^6$ .................................................. A61K 48/00
[52] U.S. Cl. ................................... 424/93.21; 435/320.1; 435/325; 435/455; 530/351; 514/44
[58] Field of Search ................................ 424/93.21, 85.1; 435/240.2, 52, 55, 65, 66, 172.3, 325; 530/351

[56] References Cited

U.S. PATENT DOCUMENTS

| 4,931,275 | 6/1990 | Shinitzky et al. | 424/88 |
| 4,963,354 | 10/1990 | Shepard et al. | 424/85.1 |
| 5,078,996 | 1/1992 | Conlon, III et al. | 424/85.1 |
| 5,098,702 | 3/1992 | Zimmerman et al. | 424/85.21 |

FOREIGN PATENT DOCUMENTS

| A 3 922 444 | 1/1991 | Germany . |
| WO 89/07136 | 8/1989 | WIPO . |
| WO 90/02806 | 3/1990 | WIPO . |
| WO 92/07573 | 5/1992 | WIPO . |
| WO 92/05262 | 4/1995 | WIPO . |

OTHER PUBLICATIONS

Mattei et al., Int. J. Cancer, 56:853–857, 1994.
Seigler et al., Annals of Surgery, 190(3):366–372, 1979.
Gilboa (Seminars in Oncology), vol. 23, 1: 101–107, 1996.
Mastrangelo et al., Seminars in Oncology, vol. 23, 1: 4–21, 1996.
Pardoll, TIPS, vol. 14: 202–208, 1993.
S.J. Russel, 1990, "Lymphokine Gene Therapy For Cancer," *Immunology Today* 11:196–200.
A.L. Asher et al., 1991, "Transduced with the Gene for Tumor Cells Transduced with the Gene for Tumor Necrosis Factor–Alpha. Evidence for Paracrine Immune Effects of Tumor Necrosis Factor Against Tumors," *J. Immunol.* 146:3227–3234.
E.R. Fearon et al., 1990, "Interleukin–2 Production by Tumor Cells bypasses T Helper Function in the Generation of an Antitumor Response," *Cell* 60:397–403.

P.T. Golumbek et al., 1991, "Treatment of Established Renal Cancer by Tumor Cells Engineered to Secrete Interleukin–4," *Science* 254:713–716.
Rosenburg, 1988, *Immun. Today* 9(2):58–62.
Oettgen & Old, 1991, "The History of Cancer Immunotherapy", *Biologic Therapy of Cancer* Devita et al., Eds. (J. Lippincott Co.) pp. 87–119.
Asher, et. al., 1991, "Murine Tumor Cells Transduced With the Gene for Tumor Necrosis Factor–α", *J. Immunol.* 146: 3227–3234.
Havell, et al., 1988, "The Antitumor Function Of Tumor Necrosis Factor (TNF)", *J. Exp. Med.* 167: 1067–1085.
Gansbacher, et al., "Retroviral Vector–mediated γ–Interferon Gene Transfer into Tumor Cells Generates Potent and Long Lasting Antitumor Immunity".
Forni, et al., 1988, "Helper strategy in tumor immunology: Expansion of helper lymphocytes and utilization of helper lymphokines for experimental and clinical immunotherapy" *Cancer and Met. Reviews* 7:289–309.
Wantanabe, et al., 1989, "Exogenous expression of mouse interferon γ cDNA in mouse neuroblastoma C1300 cells results in reduced tumorigenicity by augmented anti–tumor immunity", *Proc. Natl. Acad. Sci. USA* 86:9456–9460.
Tepper, et al., 1989, "Murine Interleukin–4 Displays Potent Anti–Tumor Activity in Vivo", *Cell* 57: 503–512.
Fearon, et al., 1990, "Interleukin–2 Production by Tumor Cells Bypasses T Helper Function in the Generation of an Antitumor Response" *Cell* 60: 397–403.
Gansbacher, et al., 1990, "Interleukin 2 Gene Transfer into Tumor Cells Abrogates Tumorigenicity and Induces Protective Immunity" *J. Exp. Med.* 172: 1217–1224.
Blankenstein, et al., 1991, "Tumor suppression after Tumor Cell–targeted Necrosis Factor α Gene Transfer", *J. Exp. Med.* 173: 1047–1052.
Teng, et al., 1991, "Long–term inhibition of tumor growth by tumor necrosis factor in the absence of cachexia or T–cell immunity" *Proc. Natl. Acad. Sci. USA* 88: 3535–3539.
Colombo, et al., 1991, "Granulocyte Colony–stimulating Factor Gene Transfer Suppresses Tumorigenicity of a Murine Adenocarcinoma In Vivo" *J. Exp. Med.* 173: 889–897.
Rollins & Sunday, 1991, "Suppression of Tumor Formation In Vivo by Expression of the JE Gene in Malignant Cells", *Mol. Cell Bio.*, 11: 3125–3131.

(List continued on next page.)

*Primary Examiner*—Bruce R. Campell
*Assistant Examiner*—Dave Trong Nguyen
*Attorney, Agent, or Firm*—Hale and Dorr LLP

[57] ABSTRACT

A method of altering the specific, systemic immune response of an individual to a target antigen by the co-administration of a cytokine an adhesion or accessory molecule and the target antigen. The target antigen may be a tumor cell, a tumor cell antigen, an infectious agent or other foreign antigen, or other antigens to which an enhanced systemic immune response is desirable. Alternatively, the antigen may be a non-foreign antigen when a suppression of a systemic immune response is desired. The resulting systemic immune response is specific for the target antigen.

9 Claims, 14 Drawing Sheets

OTHER PUBLICATIONS

Hock, et al., 1991, "Interleukin 7 Induces CD4⁺ T Cell–dependent Tumor Rejection", *J. Exp. Med.* 174: 1291–1298.

Golumbek, et al., 1991, "Treatment of Established Renal Cancer by Tumor Cells Engineered to Secrete Interleukin–4", *Science* 254: 713–716.

Foley, E.J., 1953, "Antigenic Properties of Methylcholanthrene–induced Tumors in Mice of the Strain of Origin", *Cancer Res.* 13: 835–837.

Klein, et al., 1960, "Demonstration of Resistance against Methylcholanthrene–induced Sarcomas in the Primary Autochthonous Host", *Cancer Res.* 20: 1561–1572.

Prehn & Main, 1957, "Immunity to Methylcholanthrene–Induced Sarcomas", *J. Natl. Cancer Inst.*, 18: 769–778.

Revesz, Laszlo, 1960, "Detection of Antigenic Differences in Isologous Host–Tumor Systems by Pretreatment with Heavily Irradiated Tumor Cells", *Cancer Res.* 20: 443–451.

Korman, et al., 1987, *Proc. Natl. Acad. Sci. USA*, 84: 2150–2154.

Clerici, et al., 1991, "Detection of Cytotoxic T Lymphocytes Specific For Synthetic Peptides of gp160 In HIV–Seropositive Individuals", *J. Immunol.* 146: 2214–2219.

Venet, et al., 1992, "Cytotoxic T. Lymphocyte Response Against Multiple Simian Immunodeficiency Virus $^A$ (SIV) Proteins in SIV–Infected Macaques", *J. Immunol.* 148: 2899–2908.

Hosmalin, et al., 1991, "Priming With T Helper Cell Epitope Peptides Enhances The Antibody Response To The Envelope Glycoprotein of HIV–1 In Primates", *J. Immunol.* 146: 1667–1673.

Armentano, et al., 1987, "Effect of Internal Viral Sequences on the Utility of Retroviral Vectors", *J. Virol.* 61: 1647–1650.

Sanger, et al., 1977, "DNA sequencing with chain–terminating inhibitors" *Proc. Natl. Acad. Sci. USA* 74: 5463–5467.

Yokota, et al., 1985, "Use of a cDNA expression vector for isolation of mouse interleukin 2 cDNA clones: Expression of T–cell growth–factor activity after transfection of monkey cells", *Proc. Natl. Acad. Sci. USA* 82: 68–72.

Lee, et al., 1986, "Isolation and characterization of a mouse interleukin cDNA clone that expresses B–cell stimulatory factor 1 activities and T–cell– and mast–cell–stimulating activities", *Proc. Natl. Acad. Sci. USA* 83: 2061–2065.

Campbell, et al., 1988, "Isolation, structure and expression of cDNA and genomic clones for murine eosinophil differentiation factor", *Eur. J. Biochem.* 174: 345–353.

Gough, et al., 1985, "Structure and expression of the mRNA for murine granulocyte–macrophage colony stimulating factor", *The EMBO Journal* 4: 645–653.

Horley, et al., 1989, "Molecular cloning of murine intercellular adhesion molecule (ICAM–1)", *The EMBO Journal* 8: 2889–2896.

Yagita, et al., 1988, "Molecular Cloning of the Murine Homologue of CD2", *J. Immunol.* 140: 1321–1326.

Wang, et al., 1985, "Molecular Cloning of the Complementary DNA For Human Tumor Necrosis Factor", *Science* 228: 149–154.

Gearing, et al., 1987, "Production and assay of interleukin 2", *Lymphokines and Interferons: a Practical Approach* Clemens, et al., Eds. (IRL Press, Oxford) pp. 296–299.

Hu–Li, et al., 1989, "Derivation of a T Cell Line That Is Highly Responsive to IL–4 And II–2 (CT.4R) And Of An IL–2 Hyporesponsive Mutant Of That Line (CT.4S)", *J. Immunol.* 142: 800–807.

Le, et al., 1988, "Tumor Necrosis Factor and Interleukin 1 Can Act as Essential Growth Factors in a Murine Plasmacytoma Line", *Lymphokine Research* 7: 99–106.

Dexter, et al., 1980, "Growth of Factor–Dependent Hemopoietic Precursor Cell Lines", *J. Exp. Med.* 152: 1036–1047.

Dahl & Degre, 1972, "A Micro Assay For Mouse And Human Interferon", *Acta. Pathol. Microbiol. Immunol. Scand.* 80: 863–870.

Oliff, et al., 1987, "Tumors Secreting Human TNF/Cachectin Induce Cachexia In Mice", *Cell,* 50: 555–563.

Hannum, et al., 1990, "Interleukin–1 receptor antagonist activity of an human interleukin–1 inhibitor", *Nature* 343: 336–340.

Takei, Fumio 1985, "Inhibition of Mixed Lymphocyte Response By A Rat Monoclonal Antibody To A Novel Murine Lymphocyte Activation Antigen (MALA–2)", *J. Immunol.* 134: 1403–1407.

Danos & Mulligan, 1988, "Safe and efficient generation of recombinant retroviruses with amphotropic and ecotropic host ranges", *Proc. Natl. Acad. Sci. USA* 85: 6460–6464.

Parker & Stark, 1979, "Regulation of Simian Virus 40 Transcription: Sensitive Analysis of the RNA Species Present Early in Infections by Virus or Viral DNA", *J. Virol.* 31: 360–369 360–369.

Southern & Berg, 1975, "Transformation of Mammalian Cells to Antibiotic Resistance with a Bacterial Gene Under control of the SV40 Early Region Promoter", *J. Mol. Appl. Genet.* 98: 503–517.

Southern, E.M., 1975, "Detection of Specific Sequences Among DNA Fragments Separated by Gel Electrophoresis", *J. Mol. Biol.*, 98: 503–517.

Cone, et al., 1987, "Regulated Expression of a Complete Human β–Globin Gene Encoded by a Transmissible Retrovirus Vector", *Mol. Cell Biol.* 7: 887–897.

Feinberg & Vogelstein, 1983, "A Technique for Radiolabeling DNA Restriction Endonuclease Fragments to High Specific Activity", *Anal. Biochem.* 132: 6–13.

Fidler, Isaiah J., 1975, "Biological Behavior of Malignant Melanoma Cells Correlated to Their Survival in Vivo", *Cancer Res.* 35: 218–234.

Berd, et al., 1990, "Treatment of Metastatic Melanoma With an Autologous Tumor–Cell Vaccine: Clinical and Immunologic Results in 64 Patients", *J. Clin. Oncol.* 8: 1858–1867.

Rosenberg, et al., 1977, "Use of Tumor–Infiltrating Lymphocytes and Interleukin–2 In the Immunotherapy of Patients with Metastatic Melanoma" *N. Engl. J. Med.* 146: 720–734.

Brattain, et al., 1980, "Establishment of Mouse Colonic Carcinoma Cell Lines with Different Metastatic Properties", *Cancer Res.* 40: 2142–2146.

DeLeo, et al., 1977, "Cell Surface Antigens of Chemically Induced Sarcomas of the Mouse", *J. Med. Exp.* 146: 720–734.

Murphy, et al., 1973, "A Murine Renal Cell Carcinoma", *J. Natl. Cancer Inst.* 50: 1013–1025.

Bertram, et al., 1980, "Establishment of a Cloned Line of Lewis Lung Carcinoma Cells Adapted to Cell Culture", *Cancer Letters* 11: 63–73.

Morrissey, et al., 1987, "Granulocyte–Macrophage Colony-–Stimulating Factor Augments The Primary Antibody REsponse By Enhancing the Function of Antigen–presenting Cells". *J. Immunol.* 139: 1113–1119.

Steinman, Ralph M., 1991, "The Dendritic Cell system And Its Role in Immunogenicity", *Annu. Rev. Immunol.* 9: 271–296.

Sarimento, et al., 1980, "IgG or IgM Monoclonal Antibodies Reactive with Different Determinants on the Molecular Complex Bearing LYT 2 Antigen Block T Cell–Mediated Cytolysis in the Absence of Complement", *J. Immunol.* 125: 2665–2672.

Heufler, et al., 1988, "Granulocyte/Macrophage Colony-–Stimulating Factor and Interleukin 1 Mediate the Maturation of Murine Epidermal Langerhans Cells Into Potent Immunostimulatory Dendritic Cells", *J. Exp. Med.* 167: 700–705.

Koo, et al., 1986, "The NK–1(–) Mouse: A Model To Study Differentiation of Murine NK Cells", *J. Immunol.* 137:3742–3747.

Inaba, et al., 1992, "Identification of Proliferating Dendritic Cell Precursors in Mouse Blood", *J. Exp. Med.,* 175: 1157–1167.

Hoover, et al., 1885, "Prospectively Randomized Trial of Adjuvant Active–Specific Immunotherapy for Human Colorectal Cancer", *Cancer* 55: 1236–1243.

Witmer–Pack, et al., 1987, "Granulocyte/Macrophage Colony–Stimulating Factor Is Essential for the Viability and Function of Cultured Murine Epidermal Langerhans Cells", *J. Exp. Med.* 166: 1484–1498.

Gray & Goeddel, 1983, "cloning and expression of murine immune interferon cDNA", *Proc. Natl. Acad. Sci. USA* 80: 5842–5846.

Dialynas, et al., Characterization of the Murine T. Cell Surface Molecule, Designated L3T4, Identified by Monoclonal Antibody GK1.5: Similarity of L3T4 to the Human LEU–3/T4.

Chiu, et al., 1988, "Multiple biological activities are expressed by a mouse interleukin 6 cDNA clone isolated from bone marrow stromal cells", *Proc. Natl. Acad. Sci. USA* 85: 7099–7103.

Mulligan, Richard C., 1991, "Gene Transfer and Gene Therapy—Principles, Prospects, and Perspective", *Etiology of Human Disease at the DNA Level* ed. Lindsten and Pettersson Raven Press, Ltd.

Coligan, et al. 1991 *Current Protocols in Immunology* (Greene Publishing Associates and Wiley Interscience).

Sambrook, et al., 1989 *Molecular Cloning: A Laboratory Manual* (Cold Spring Harbor Press).

Gilboa, E. "Retrovirus vectors and their uses in molecular biology," *Bioessays* 5(6):252–257 (1986).

Lim, B. et al. "Retrovirus–mediated gene transfer of human adenosine deaminase; expression of functional enzyme in murine hematopoietic stem cells in vivo," *Molec. Cell. Biol.* 7(10):3459–3465 (1987).

Wilson, J. et al. "Correction of the genetic defect in hepatocytes from the Watanabe heritable hyperlipidemic rabbit," *Proc. of the Natl. Acad. of Sci.* 85:4421–4425 (1988).

Israel et al. "Retroviral–mediated transfer and amplification of a functional human factor VIII gene," *Blood* 75(5):1074–1080 (1990).

Morgenstern et al. "Advanced mammalian gene transfer: high titre retroviral vectors with multiple drug selection markers and a complementary helper–free packaging cell line," *Nucleic Acids Research* 18(12):3587–3596 (1990).

Hurford Jr., R. et al. "Gene therapy of metastatic cancer by in vivo retroviral gene targeting," *Nat. Genet.* 10(4):430–435 (1995).

REGULATION OF SYSTEMIC IMMUNE RESPONSES UTILIZING CYTOKINES AND ANTIGENS

CROSS REFERENCE TO RELATED APPLICATIONS

This is a continuation-in-part of U.S. application Ser. No. 08/265,554, filed Jun. 23, 1994, now U.S. Pat. No. 5,637,483, which is a file-wrapper-continuation of U.S. application Ser. No. 07/956,621, filed Oct. 5, 1992, abandoned, which is a continuation-in-part of U.S. application Ser. No. 07/771,194, filed Oct. 4, 1991, abandoned, the disclosures of which are incorporated herein by reference.

I. FIELD OF THE INVENTION

The present invention in all of its associated aspects relates to a method of altering an individual's immune response to a target antigen or antigens. More particularly, the present invention is concerned with co-administering a target antigen and at least one cytokine, in such a manner as to either increase or decrease the individual's immune response. Possible antigens include tumor cells, tumor cell antigens, infectious agents, foreign antigens, or non-foreign components. The invention also relates to methods and combinations for co-administering the antigens and the cytokines.

II. BACKGROUND OF THE INVENTION

The immune system plays a critical role in the pathogenesis of a wide range of important diseases and conditions, including infection, autoimmunity, allograft rejection and neoplasia. The shortcomings of the immune system in these disorders can be broadly considered as either the failure to develop a sufficiently potent response to a deleterious target or the inappropriate generation of a destructive response against a desirable target. Standard medical treatments for these diseases, including chemotherapy, surgery and radiation therapy, have clear limitations with regard to both efficiency and toxicity. While prevention of the disease or condition would be ideal, these approaches typically have met with little success. New strategies based on specific manipulation of the immune response are greatly needed.

III. DESCRIPTION OF THE PRIOR ART

For the convenience of the reader, the references referred to in the text are listed numerically in parentheses. These numbers correspond to the numerical references listed in the appended bibliography. By these references, they are hereby expressly incorporated by reference herein.

The use of autologous cancer cells as vaccines to augment anti-tumor immunity has been explored throughout this century (1). However, the immunogenicity of cancer cells is generally too weak to elicit a pronounced immune reaction sufficient to overcome the disease. Patient responses to these "raw" vaccines have generally been only partial and relatively shortlived. Strategies to improve the efficacy of such vaccinations, including the use of non-specific immunostimulants such as BCG and Corynebacterium parvum, have resulted in little improvement.

One approach has been to increase the immunogenicity of tumor cells by treating the cells in different ways. For example, U.S. Pat. No. 4,931,275 describes using as a vaccine either cells treated with pressure or cholesteryl hemisuccinate, or plasma membranes or membrane proteins from these cells. These methods attempt to enhance the exposure of surface antigens to render the antigens more immunogenic.

Another approach focuses on the interaction of cytokines and the immune system. Cytokines and combinations of cytokines have been shown to play an important role in the stimulation of the immune system. For example, U.S. Pat. No. 5,098,702, describes using combinations of TNF, IL-2 and IFN-$\beta$ in synergistically effective amounts to combat existing tumors. U.S. Pat. No. 5,078,996 describes the activation of macrophage nonspecific tumoricidal activity by injecting recombinant GM-CSF to treat patients with tumors.

A further expansion of this approach involves the use of genetically modified tumor cells to evaluate the effects of cytokines on tumorigenicity. Since the doses of cytokines necessary to effect tumor development are often systemically toxic, direct treatment of patients is frequently not feasible (see, for example, (2) and (3)). Therefore, other methods of cytokine delivery are being developed. Studies show that localized high concentrations of certain cytokines, delivered by genetically modified cells, lead to tumor regression (4, 5). Such studies show that the transduction of murine tumor cells with various cytokine genes can lead to the rejection of the genetically modified cells by syngeneic hosts. For example, growth of malignant mouse neuroblastoma cells injected into mice was strongly suppressed when the cells constitutively expressed $\gamma$-IFN at high levels (4,6). Injection of mammary adenocarcinoma tumor cells expressing IL-4, mixed with a variety of nontransfected tumor cells, inhibited or prevented tumor formation of all types (7). Similar results are seen for IL-2 (8,9), TNF-$\alpha$ (2,10,11), G-CSF (12), JE (13), and IL-7 (14).

Yet another approach involves the use of genetically modified tumor cells as vaccines. Injection of tumor cells expressing IL-2 not only suppresses tumor formation initially but confers a short-lived systemic immunity as well, thus allowing the mice to reject a subsequent challenge of tumor cells (8). For example, mice were able to reject tumor cells injected two weeks after the vaccine but not at four weeks. This immunity is tumor specific in that other tumors grew normally when injected two weeks after the initial vaccine injection (8). Similar results are seen with TNF-$\alpha$, where animals that experience initial tumor rejection were challenged two weeks later and did not develop new tumors for at least 40 days (2). A somewhat longer systemic immunity is seen with IFN-$\gamma$, with mice vaccinated with IFN-$\gamma$ producing tumor cells successfully rejecting unmodified tumor cells injected 6 weeks later.

The efficacy of these vaccines to stimulate the immune system to attack a previously growing tumor, which is the more desirable trait of the vaccine, is not as clear. For IL-4, IFN-$\gamma$, and IL-2, injection of cytokine-producing tumor cells did not affect the growth of non-modified tumor cells at a different site on the animal. It is undocumented whether the non-modified tumor cells were already established tumors, or cells that were simultaneously injected with the modified cytokine producing tumor cells (7, 4, 9 and 8, respectively). In a single recent case, tumor cells engineered to secrete IL-4 successfully mediated rejection of established renal cancer cells (15).

While these studies may suggest the potential use of gene transfer as a means of augmenting anti-tumor immunity, there are many problems with these systems. First of all, treating already existing cancers is one of the primary goals of the research. While the vaccine aspect of these methods is very important, particularly in precancerous patients, for example, or in cases where certain individuals acquire defined cancers (such as AIDS patients), the ability to systemically treat existing cancers is particularly appealing.

Another problem is the relatively short period of efficacy for the vaccine; generally these vaccines have been effective only for tumor challenges at less than 2 to 6 weeks after vaccination.

Also, the mechanism by which engineered cytokine expression promotes such immunity is currently unclear. To date, for instance, none of the gene transfer studies have compared the efficacy of such live vaccines to the immune response induced simply by the vaccination of hosts with non-transduced cells, either inactivated by γ-irradiation or other means, or by non-transduced cells that are surgically remove after implantation. This would appear to be quite important, since a large body of literature indicates that often such vaccination schemes alone can stimulate potent antitumor immunity (16, 17, 18, 19).

IV. SUMMARY OF THE INVENTION

The present invention is based on the determination that tumor cells expressing certain cytokines and combinations of cytokines can confer long term specific systemic immunity to individuals receiving injections of such cells. From that finding, the present invention provides for the regulation, either in a stimulatory or suppressive way, of an individual's immune response to a useful antigen.

The method of the present invention is useful for preventative purposes as well as therapeutic applications. That is, it is useful to protect an individual against development or progression of a tumor, bacterial or viral infection such as AIDS, rejection of transplanted tissue, or autoimmune condition. The present invention also will find utility in the reversal or suppression of an existing tumor, condition or disease, such as established tumors, bacterial or viral infections such as AIDS, transplanted tissue rejection, or autoimmune responses. In addition, the present invention finds utility in the treatment of chronic and life threatening infections, such as the secondary infections associated with AIDS, as well as other bacterial, fungal, viral, parasitic and protozoal infections. A particular advantage of the present invention is that the cytokines may be selected to optimize effects in the individual and thus maximize the desired result.

As one aspect of the present invention, there is disclosed a method for regulating the immune response of an individual to a target antigen. The regulation is achieved by co-administering to the individual the target antigen and at least one cytokine, adhesion or accessory molecules or combinations thereof, in such a manner that there is a systemic immune response. The antigen and the cytokine, adhesion or accessory molecules or combinations thereof, are co-administered in a therapeutically effective amount, which results in the systemic immune response.

Another aspect of the present invention utilizes cells which express the target antigen and at least two cytokines, either naturally or as a result of genetic engineering, that can be administered to an individual whose immune response to the target antigen is to be regulated. For example, a tumor cell of the type against which an enhanced immune response is desired can be engineered to express the cytokines to be administered. The resulting genetically engineered tumor cell is used as a vaccine, to protect against future tumor development or as a delivery vehicle to result in the reversal of previously existing tumors.

Specific aspects of the present invention utilize tumor cells expressing the two cytokines GM-CSF and IL-2, and utilizes melanoma cells as the tumor cells to be modified.

Another aspect of the present invention relates to the use of modified tumor cells, expressing cytokines, which are irradiated or rendered proliferation incompetent prior to administration to an individual. These irradiated, modified cells are administered in therapeutically effective amounts. Administration of these cells results in the regulation, either as a stimulatory manner or a suppressive manner, of the individual's systemic immune response. Of particular utility are tumor cells expressing GM-CSF, and specifically melanoma cells expressing GM-CSF. Also of use in the present invention are irradiated tumor cells expressing GM-CSF IL-4, IL-6, CD2 and ICAM.

Human clinical studies are also described that involve autologous primary and/or secondary melanoma or renal cell carcinoma cells which have been transduced to express the cytokine GM-CSF which have been irradiated to an extent that the cells are no longer capable of sustained cell division, and injected into the original donor.

In other aspects, the invention relates to the use of modified tumor cells expressing cytokines for the reversal or suppression of pre-existing tumors. The tumor cells may express two cytokines, for example IL-2 and GM-CSF, or three cytokines, for example IL-2, GM-CSF, and TNF-α. The third cytokine may also be IL-4, CD2 or ICAM. The tumor cells may also be irradiated or rendered proliferation incompetent by other means prior to administration.

In another aspect, the present invention relates to the use of retroviral vectors to genetically engineer the cytokine-expressing tumor cells. The invention may utilize a single infection of a tumor cell by a retroviral vector encoding a cytokine, or it may utilize multiple infections by retroviral vectors encoding different cytokines.

A variety of retroviral vectors may be used. The MFG, α-SGC, pLJ, and pEm vectors abandoned, (and derivatives thereof, e.g. MFG-S) are more fully disclosed in U.S. Ser. No. 07/786,015, filed Oct. 31, 1991 abandoned (PCT/US91/08121, filed Oct. 31, 1991), incorporated herein by reference, and will find particular utility in the present invention.

V. DESCRIPTION OF THE DRAWINGS

FIG. 1 schematically represents the recombinant retroviral vectors useful in the present invention. FIG. 1A shows a detailed representation of the MFG vector. FIG. 1B shows the pLJ vector. FIG. 1C shows the pEm vector. FIG. 1D shows the A-SGC vector.

Figure 2A:
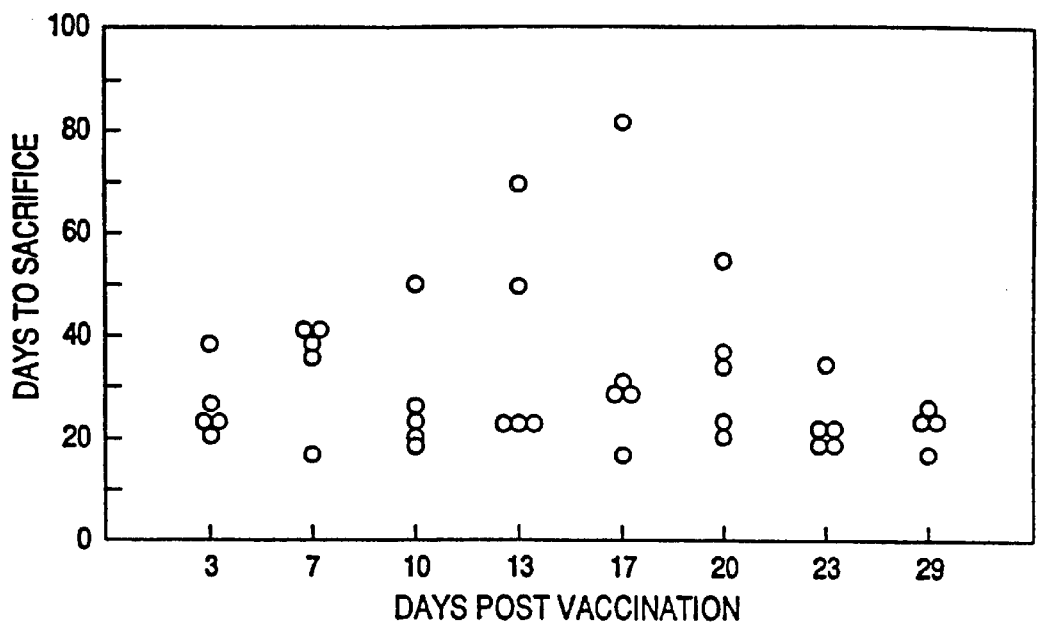
Figure 2B:
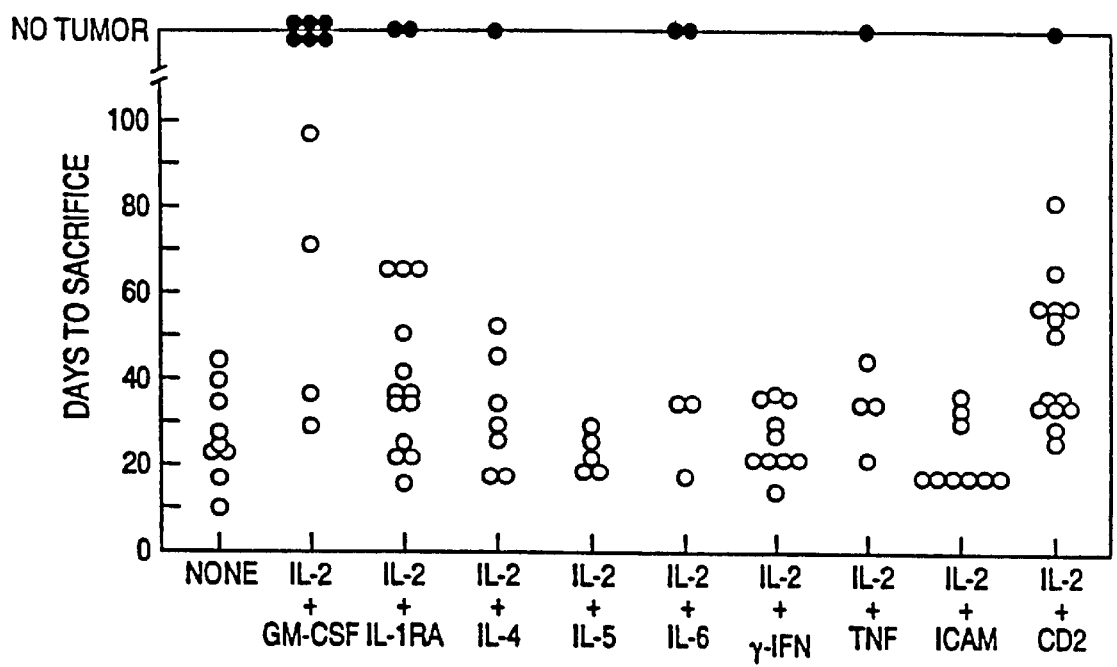

FIG. 2:

FIG. 2A graphically represents the ability of B16 melanoma cells expressing IL-2 to protect against subsequent challenge with wild-type B16 melanoma cells at various times after vaccination FIG. 2B graphically represents the ability of B16 melanoma cells expressing IL-2 and a second cytokine (as indicated) after vaccination to protect against challenge with wild-type B16 melanoma cells. The symbol ○ represents the animals that succumbed to tumor challenge and the symbol ● represents the animals protected from tumor challenge.

Figure 2C:
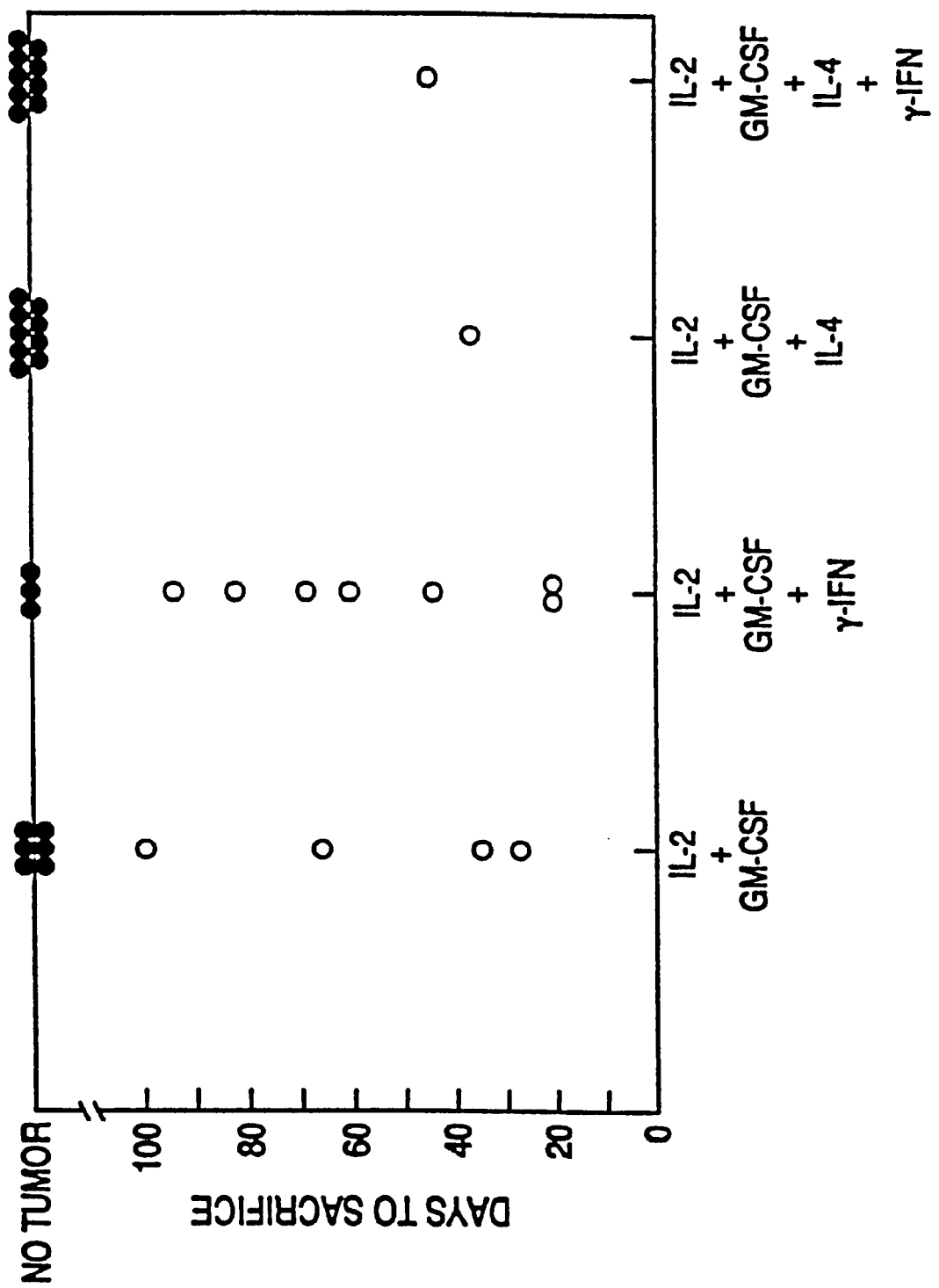

FIG. 2C graphically represents the ability of B16 melanoma cells expressing IL-2 and GM-CSF and a third cytokine (as indicated) to protect against subsequent challenge with wild-type B16 melanoma cells.

Figure 3A:
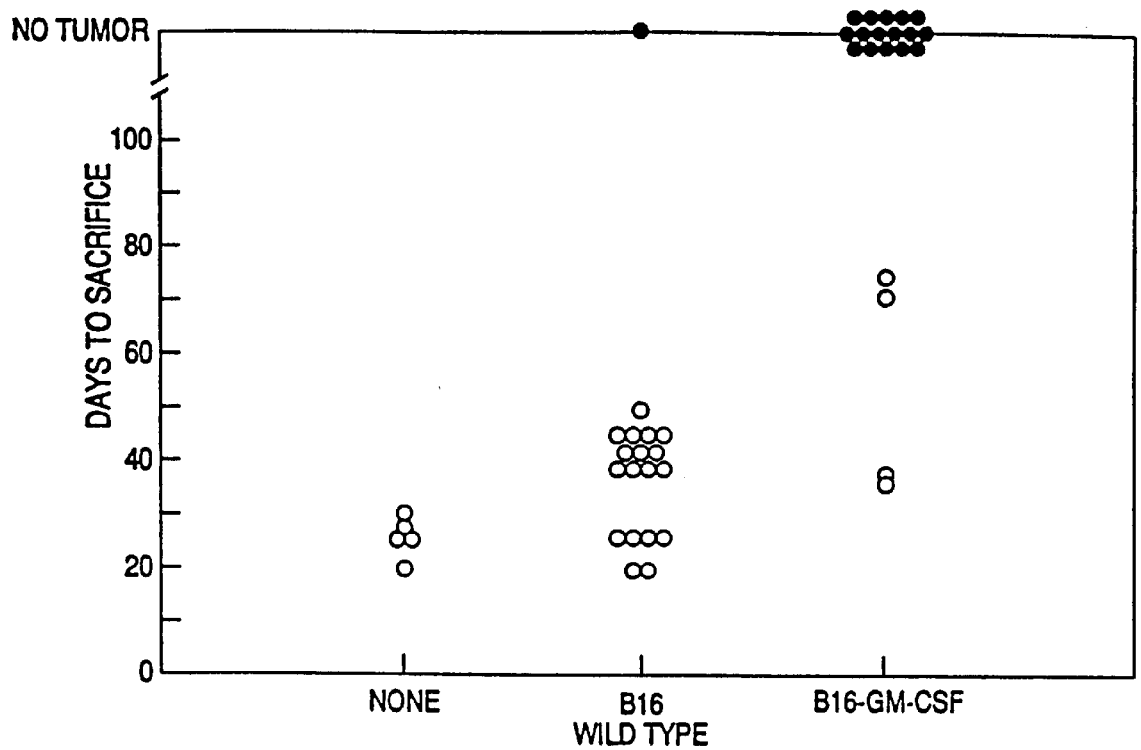

FIG. 3:

FIG. 3A graphically represents the ability of irradiated B16 melanoma cells expressing GM-CSF to protect against challenge with wild-type B16 melanoma cells. The symbol ○ represents the animals that succumbed to tumor challenge and the symbol ● represents the animals protected from tumor challenge.

Figure 3B:
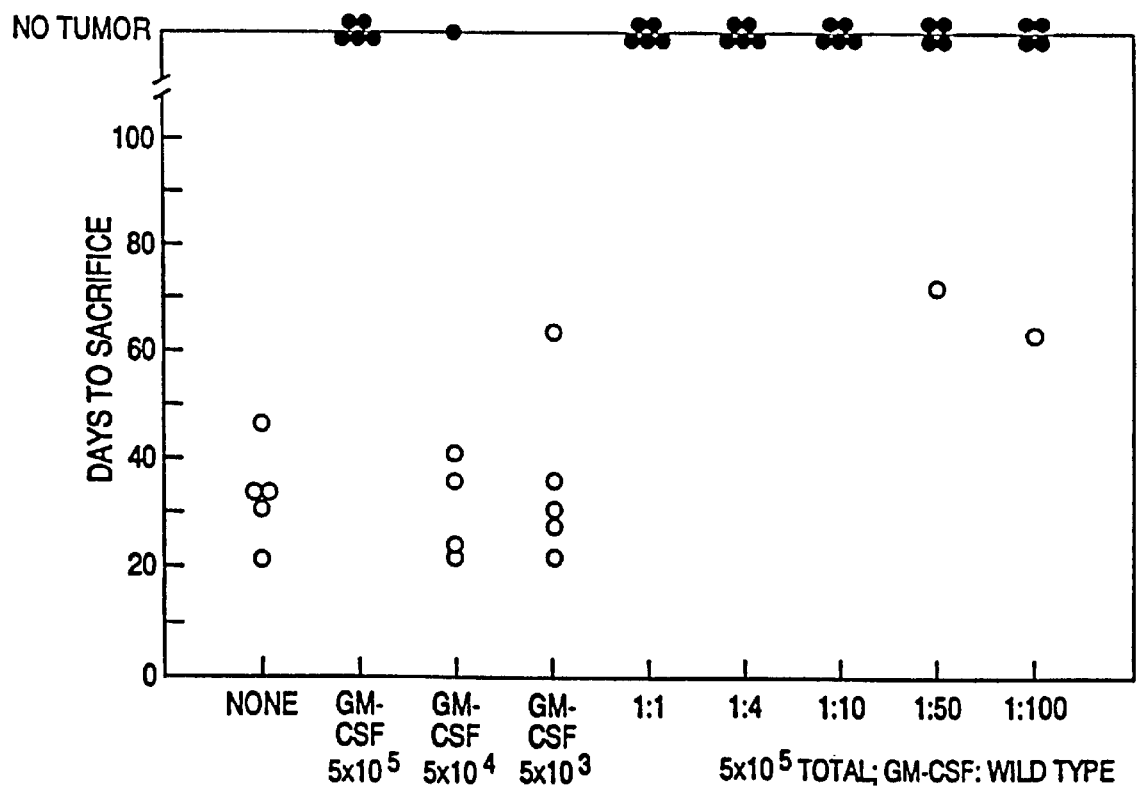

FIG. 3B graphically represents the ability of irradiated B16 melanoma cells expressing GM-CSF to protect against challenge with wild-type B16 melanoma cells either at varying doses or when mixed with non-transduced B16 melanoma cells. The symbol ○ represents the animals that succumbed to tumor challenge and the symbol ● represents the animals protected from tumor challenge.

Figure 3C:
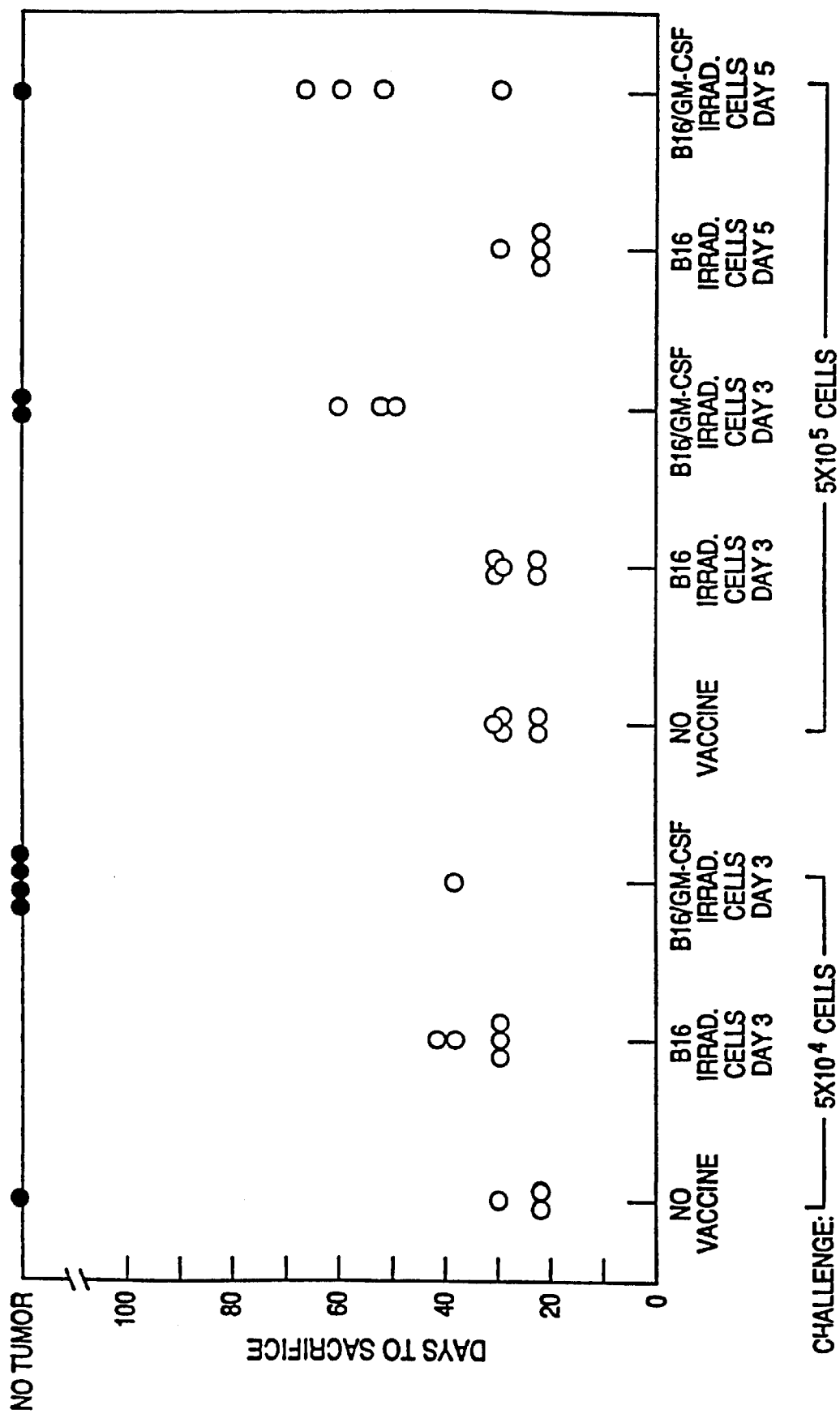

FIG. 3C graphically represents the ability of irradiated B16 melanoma cells expressing GM-CSF to increase the immune response after inoculation with live non-transduced B16 melanoma cells (pre-established tumor) as indicated. The symbol ○ represents the animals that succumbed to tumor challenge and the symbol ● represents the animals protected from tumor challenge.

Figure 4:
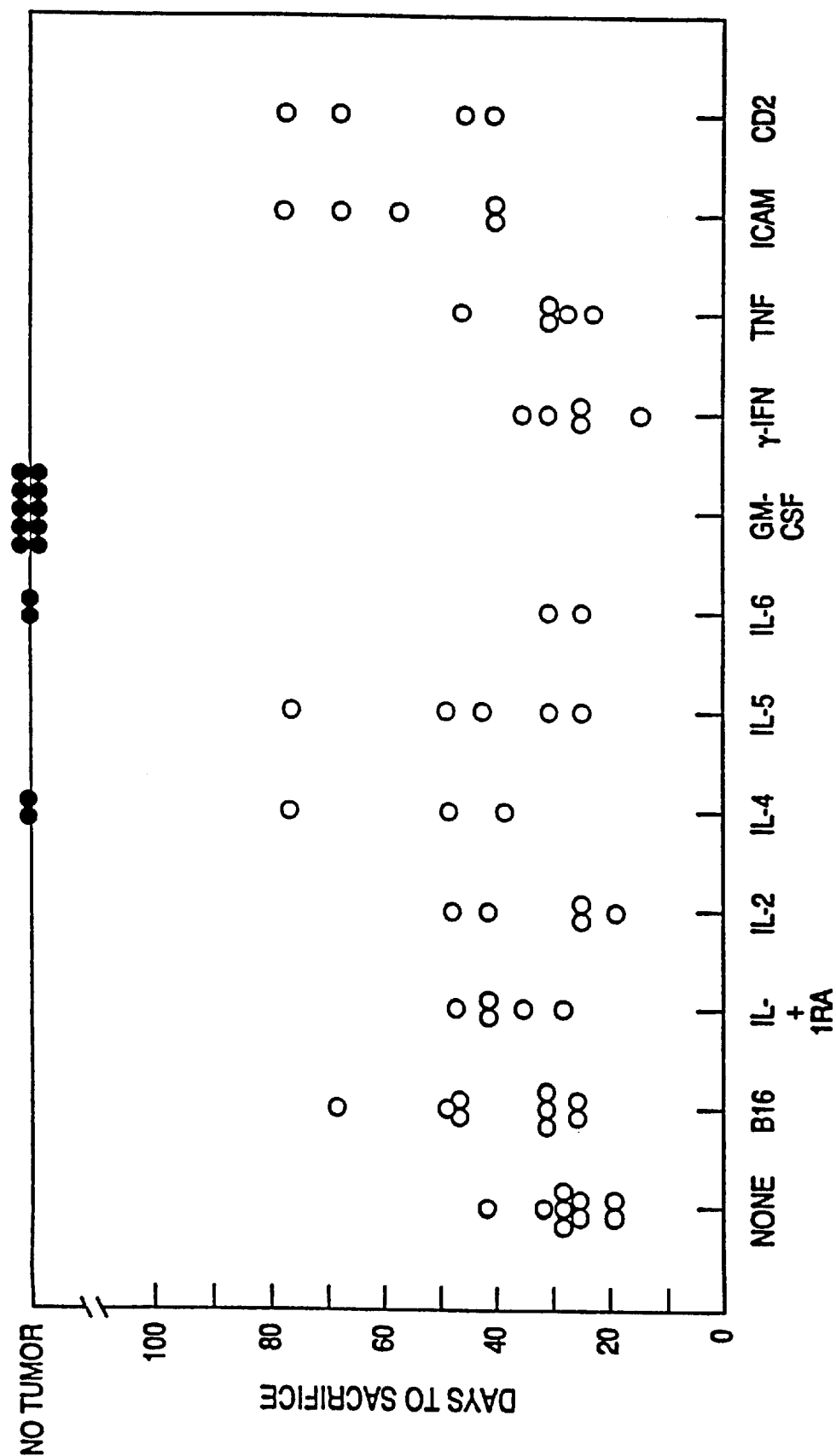
Figure 5A:
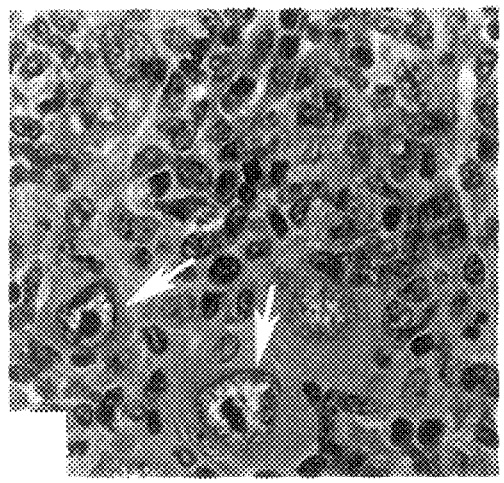
Figure 5B:
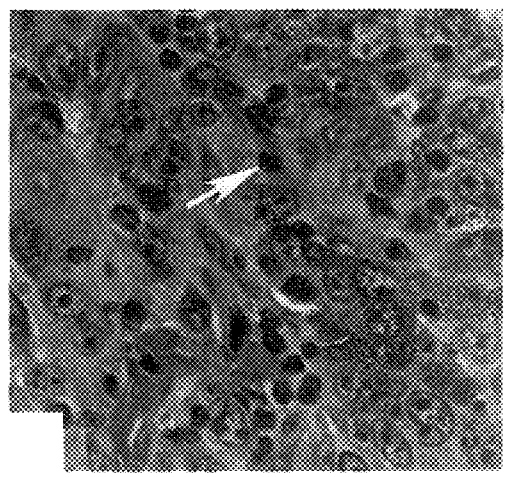
Figure 5C:
Figure 5D:
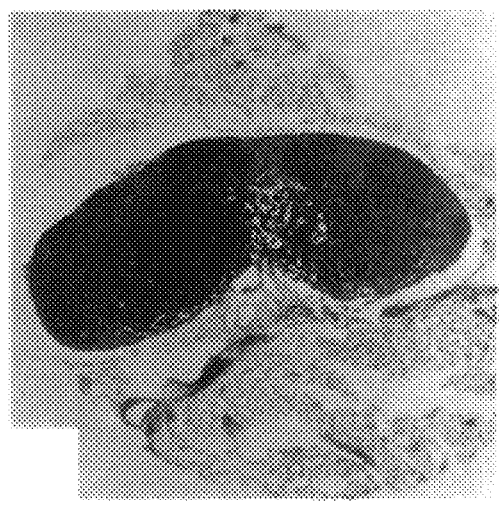
Figure 5E:
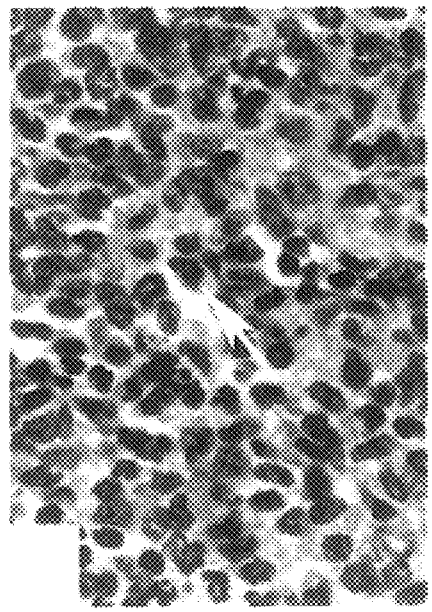
Figure 5F:
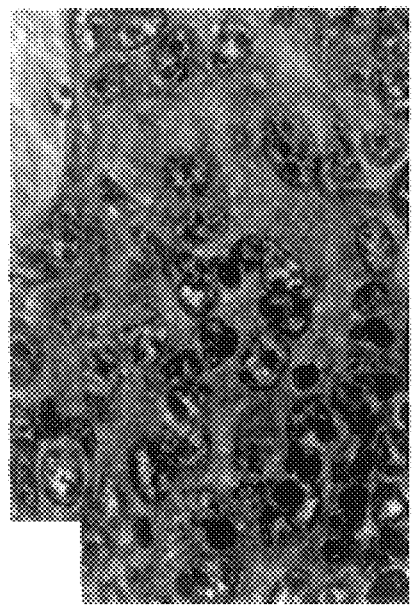
Figure 5G:
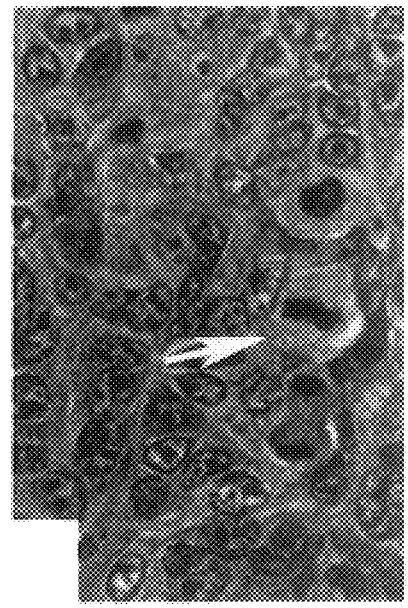

FIG. 4 graphically represents the ability of irradiated B16 melanoma cells expressing a cytokine (as indicated) to protect against subsequent challenge with wild-type B16 melanoma cells. The symbol ○ represents the animals that succumbed to tumor challenge and the symbol ● represents the animals protected from tumor challenge.

FIG. 5 pictorially represents the histological analysis of the site of B16 melanoma vaccination. FIG. 5A shows the site of irradiated GM-CSF transduced tumor vaccination. FIG. 5B shows the site of irradiated non-transduced tumor vaccination site. FIG. 5C shows the draining lymph node from the irradiated GM-CSF transduced tumor vaccination. FIG. 5D shows the draining lymph node from the irradiated non-transduced tumor vaccination. FIG. 5E shows the challenge site of a mouse vaccinated with irradiated GM-CSF transduced tumor cells. FIG. 5F shows the challenge site of a mouse vaccinated with irradiated non-transduced tumor cells. FIG. 5G shows the challenge site in a naive mouse.

Figure 6A:
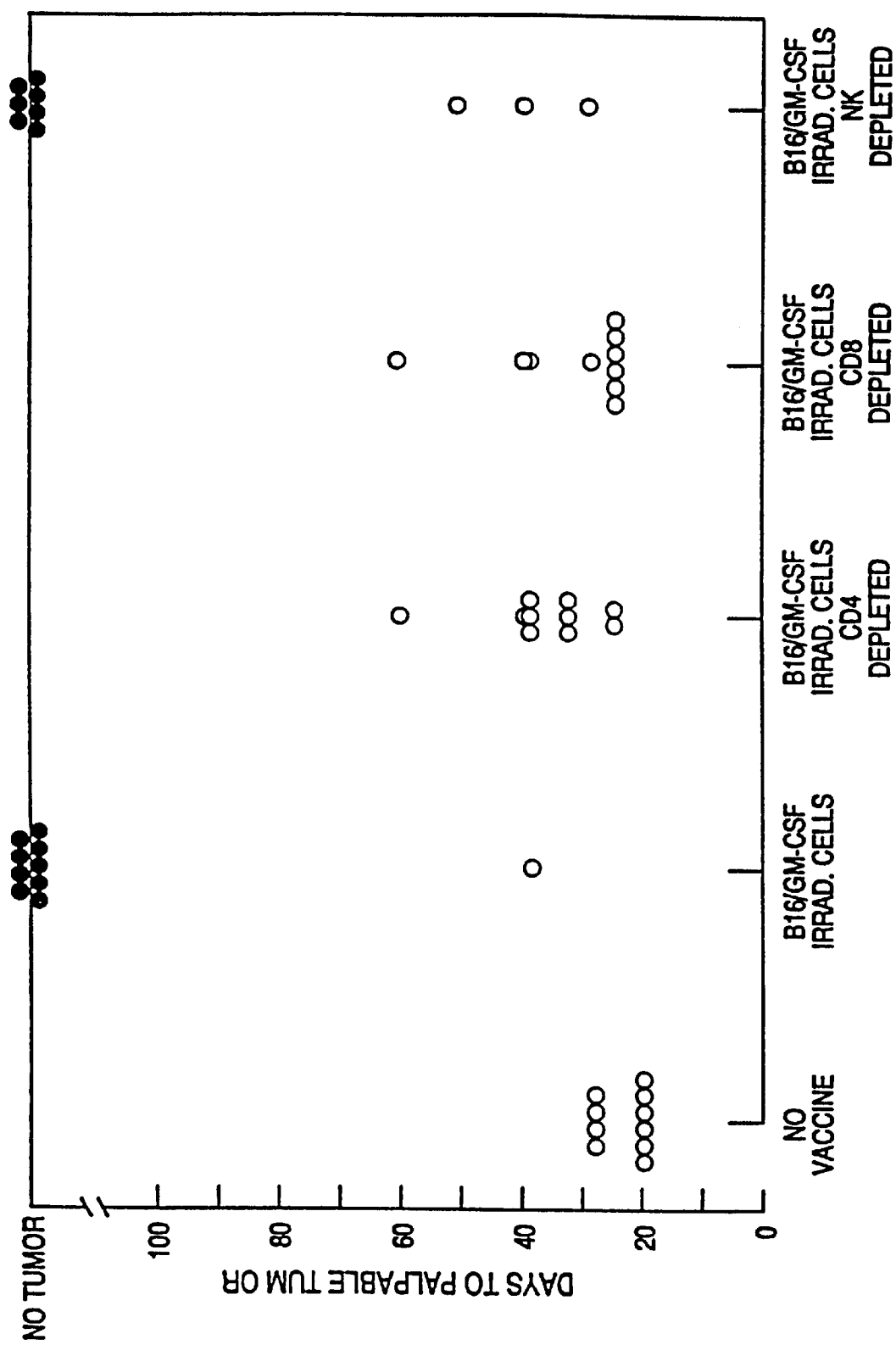

FIG. 6:

FIG. 6A graphically represents the contribution of lymphocyte subsets to systemic immunity gene-rated by irradiated GM-CSF transduced B16 melanoma cells. The symbol ○ represents the animals that succumbed to tumor challenge and the symbol ● represents the animals protected from tumor challenge.

Figure 6B:
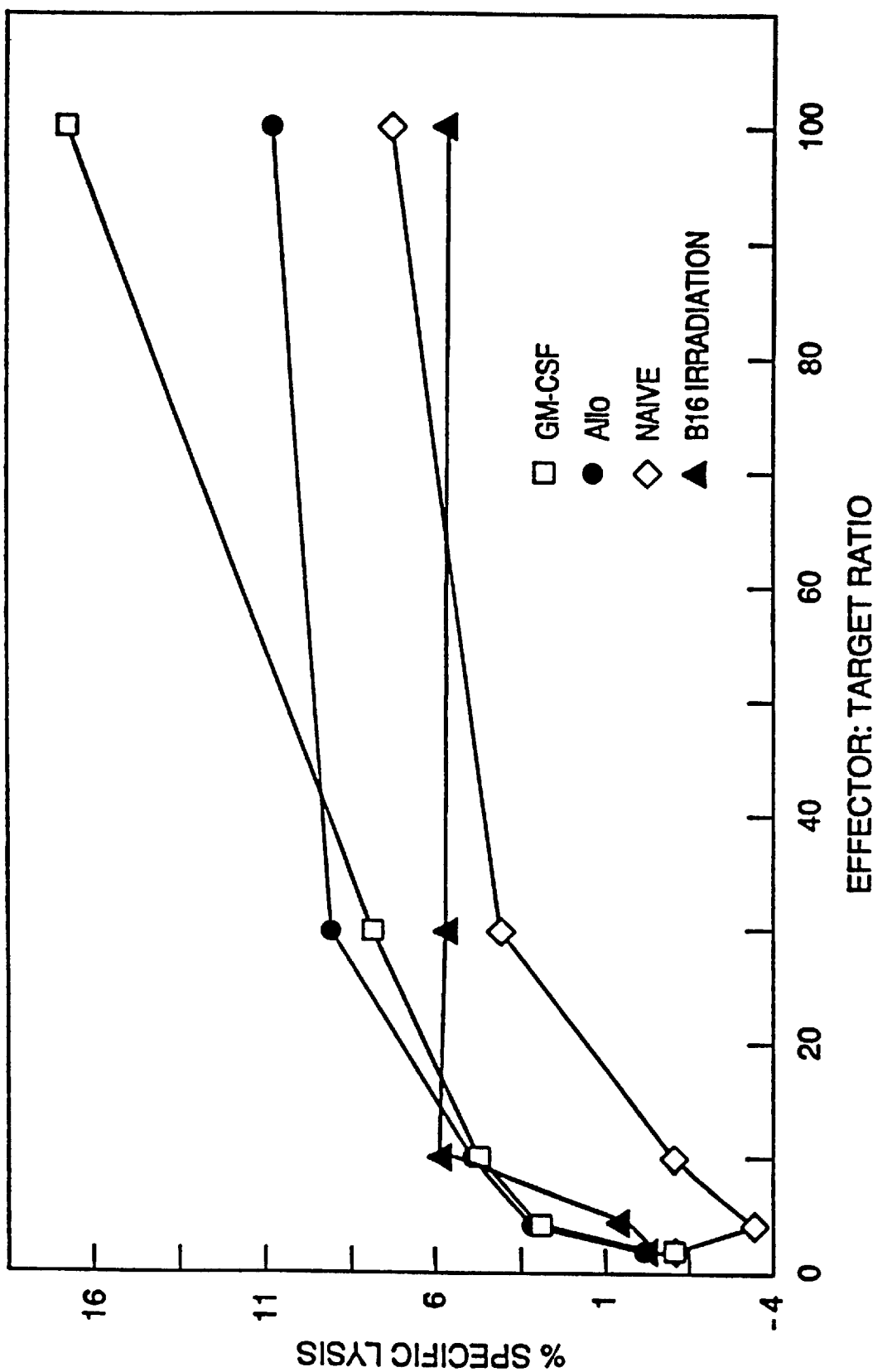

FIG. 6B graphically represents the CD8 blockable CTL activity, determined by a 4 hour $^{51}$Cr release assay on gamma-interferon treated B16 target cells at various effector:target ratios. Fourteen days after vaccination with either irradiated GM-CSF transduced or non-transduced B16 cells, splenocytes were harvested and stimulated in vitro for 5 days with gamma-interferon treated B16 cells.

Figure 7:
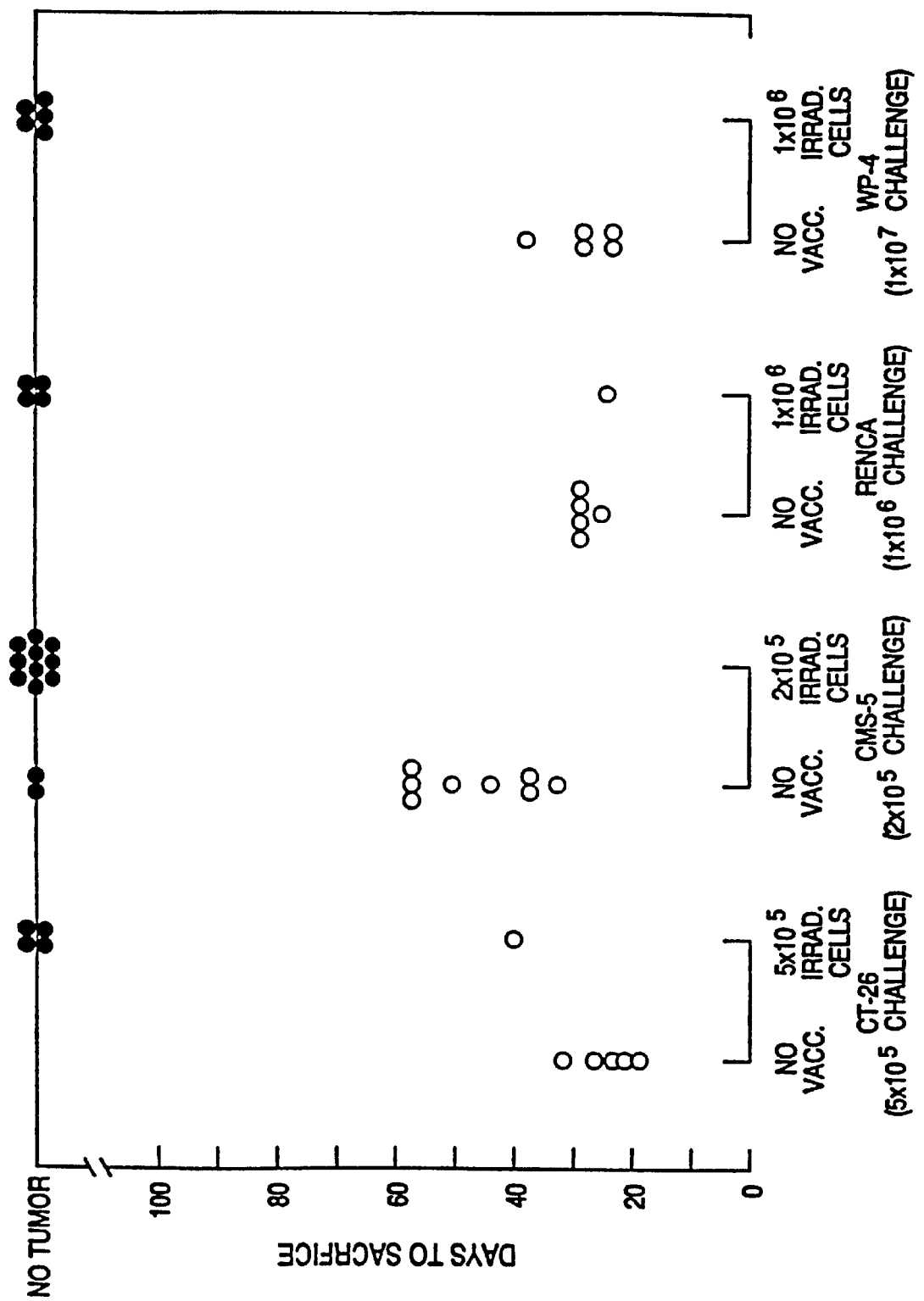

FIG. 7 graphically represents the immunogenicity of irradiated, non-transduced murine tumor cell lines used in previous cytokine transfection studies. The symbol ○ represents the animals that succumbed to tumor challenge and the symbol ● represents the animals protected from tumor challenge.

Figure 8:
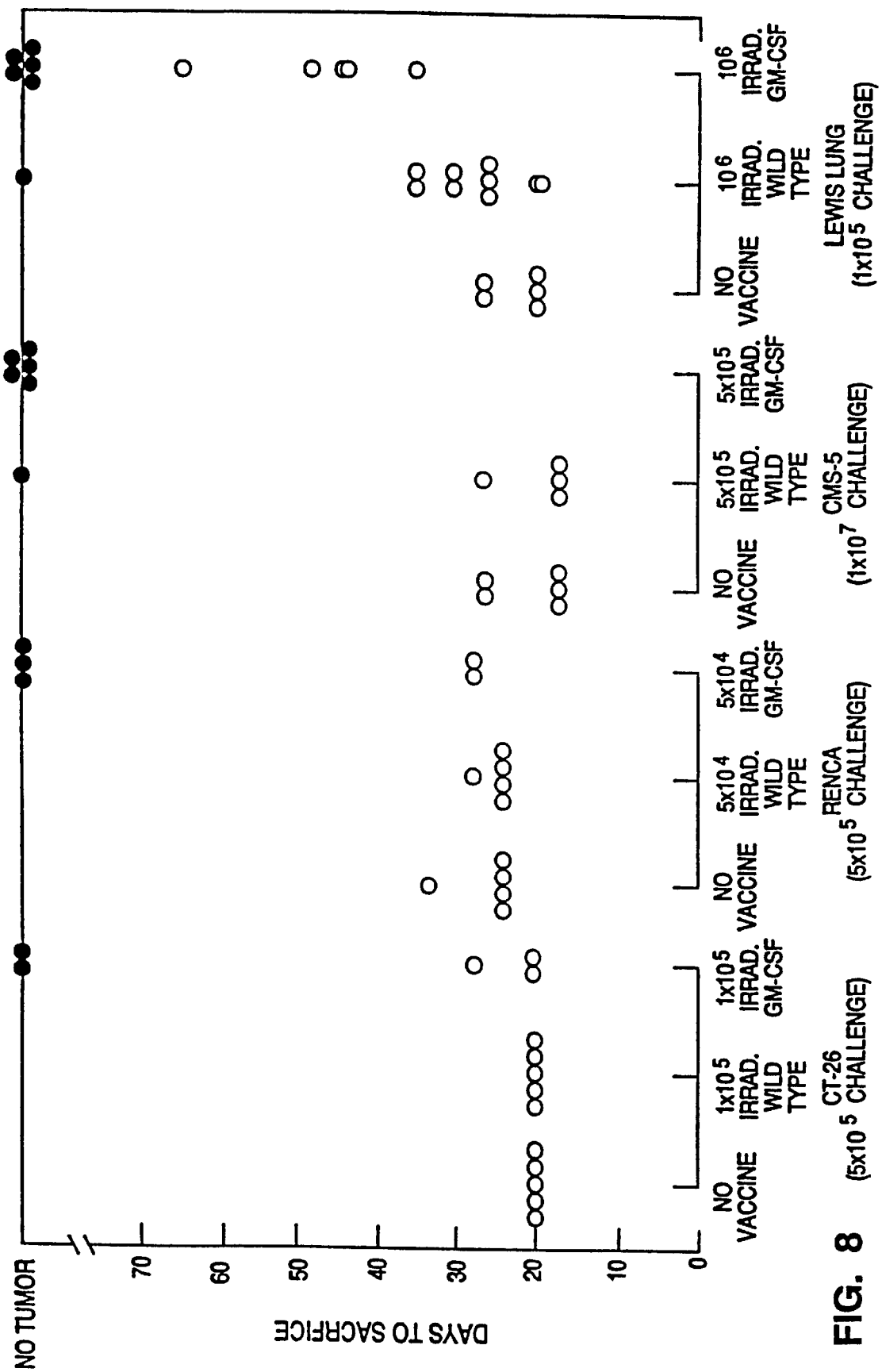

FIG. 8 graphically represents the ability of GM-CSF to enhance the systemic immunity of irradiated tumor cells of the types indicated relative to non-transduced irradiated tumor cells. The symbol ○ represents the animals that succumbed to tumor challenge and the symbol ● represents the animals protected from tumor challenge.

Figure 9:
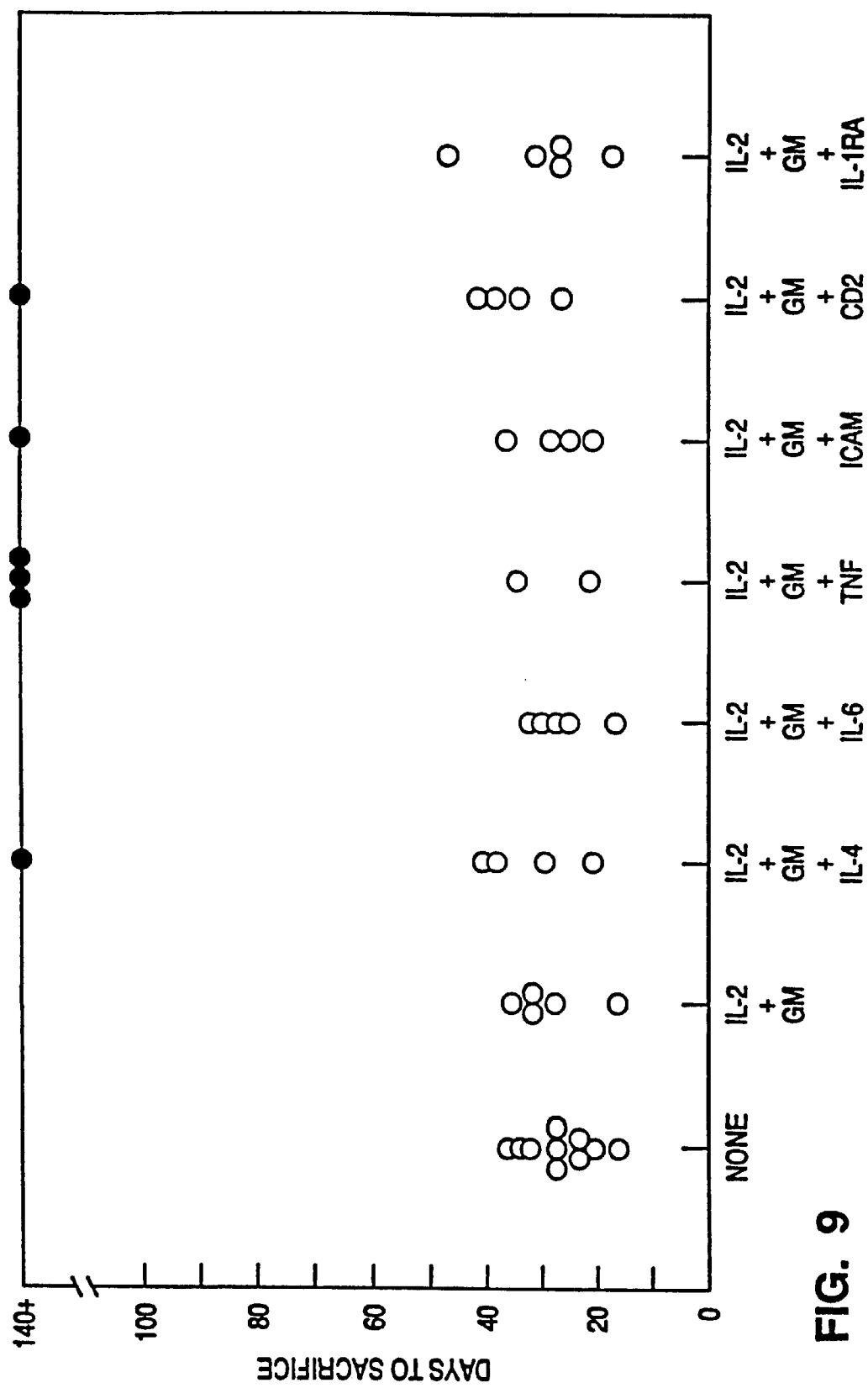

FIG. 9 graphically represents the effect of B16 melanoma cells expressing IL-2, GM-CSF and a third cytokine, as indicated, on a pre-existing tumor. The symbol ○ represents the animals that succumbed to tumor challenge and the symbol ● represents the animals protected from tumor challenge.

Figure 10:
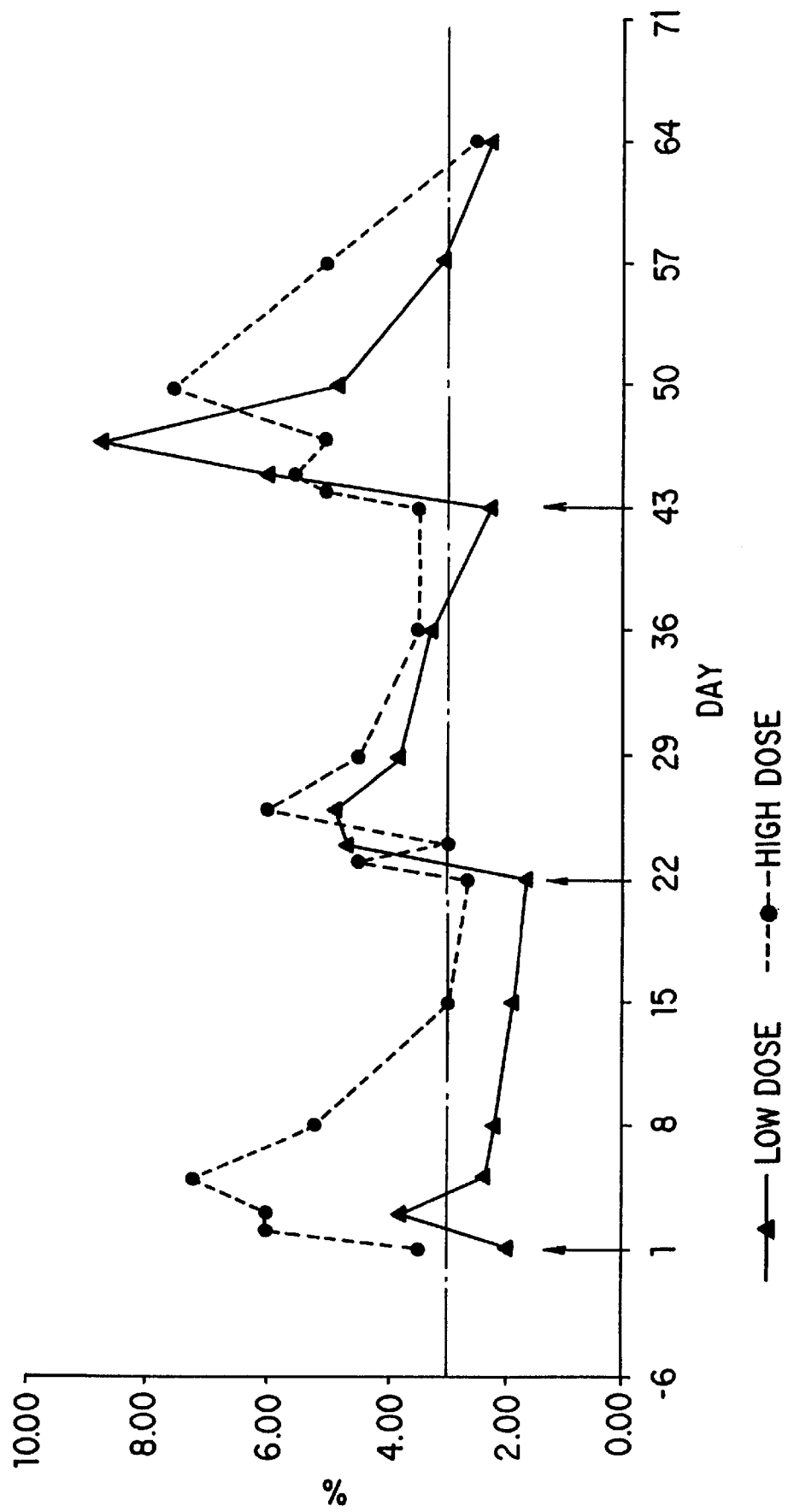

FIG. 10 shows a time course of the average percentage of eosinophils in the test subjects during the 64 day period in which the transduced melanoma cells were injected into the patients. The arrows indicate that the injections were made at days 1, 22, and 43. The circles represent the average data of the low dose patients and the triangles indicate the average data of the high dose patients.

VI. DETAILED DESCRIPTION OF THE INVENTION

6.1. Definitions

By the term "regulating the immune response" or grammatical equivalents, herein is meant any alteration in any cell type involved in the immune response. The definition is meant to include an increase or decrease in the number of cells, an increase or decrease in the activity of the cells, or any other changes which can occur within the immune system. The cells may be, but are not limited to, T lymphocytes, B lymphocytes, natural killer (NK) cells, macrophages, eosinophils, mast cells, dendritic cells, or neutrophils. The definition encompasses both a stimulation or enhancement of the immune system to develop a sufficiently potent response to a deleterious target, as well as a suppression of the immune system to avoid a destructive response to a desirable target. In the case of stimulation of the immune system, the definition includes future protection against subsequent tumor challenge.

By the term "cytokine" or grammatical equivalents, herein is meant the general class of hormones of the cells of the immune system, both lymphokines and monokines, and others. The definition is meant to include, but is not limited to, those hormones that act locally and do not circulate in the blood, and which, when used in accord with the present invention, will result in an alteration of an individual's immune response. The cytokine can be, but is not limited to, IL-l($\alpha$ or $\beta$), IL-2, IL-3, IL-4, IL-5, IL-6, IL-7, IL-8, IL-9, IL-10, IL-11, IL-12, GM-CSF, M-CSF, G-CSF, LIF, LT, TGF-$\beta$, $\gamma$-IFN (or $\alpha$ or $\beta$-IFN), TNF-$\alpha$, BCGF, CD2, or ICAM. Descriptions of the aforementioned cytokines as well as other applicable immunomodulatory agents may be found in "Cytokines and Cytokine Receptors", A. S. Hamblin, 1993, (D. Male, ed., Oxford University Press, New York, N.Y.), or the "Guidebook to Cytokines and Their Receptors", 1995, N. A. Nicola, ed. (Oxford University Press, New York, N.Y.) herein incorporated by reference.

Where therapeutic use in humans is contemplated, the cytokines or hormones will preferably be substantially similar to the human form of the protein or have been derived from human sequences (i.e., of human origin).

Additionally, cytokines of other mammals with substantial homology to the human forms of IL-2, GM-CSF, TNF-$\alpha$, and others, will be useful in the invention when demonstrated to exhibit similar activity on the immune system. Similarly, proteins that are substantially analogous to any particular cytokine, but have relatively minor changes of protein sequence, will also find use in the present invention. It is well known that some small alterations in protein sequence may be possible without disturbing the functional abilities of the protein molecule, and thus proteins can be made that function as cytokines in the present invention but differ slightly from currently known sequences. Thus, proteins that are substantially similar to any particular cytokine, but have relatively minor changes of protein sequence, will also fine use in the present invention.

Finally, the use of either the singular or plural form of the word "cytokine" in this application is not determinative and should not limit interpretation of the present invention and claims. In addition to the cytokines, adhesion or accessory molecules or combinations thereof, may be employed alone or in combination with the cytokines.

By the term "antigen from a tumor cell" or grammatical equivalents thereof, herein is meant any protein, carbohydrate or other component capable of eliciting an immune response. The definition is meant to include, but is not limited to, using the whole tumor cell with all of its associated antigens as an antigen, as well as any component separated from the body of the cell, such as plasma membranes, proteins purified from the cell surface or membrane, or unique carbohydrate moieties associated with the cell surface. The definition also includes those antigens from the surface of the cell which require special treatment of the cells to access.

By the term "systemic immune response" or grammatical equivalents herein, is meant an immune response which is not localized, but affects the individual as a whole, thus allowing specific subsequent responses to the same stimulus.

By the term "co-administering" or grammatical equivalents herein, is meant a process whereby the target antigen and the selected cytokine or cytokines are encountered by the individual's immune system at essentially the same time. The components need not be administered by means of the same vehicle. If they are administered in two separate vehicles, they must be administered sufficiently closely, both in time and by route of administration, that they are encountered essentially simultaneously by the individual's immune system to achieve the desired specificity.

By the term "reversal of an established tumor" or grammatical equivalents herein is meant the suppression, regression, partial or complete disappearance of a preexisting tumor. The definition is meant to include any diminution in the size, potency, growth rate, appearance or feel of a pre-existing tumor.

One of ordinary skill will appreciate that, from a medical practitioner's or patient's perspective, virtually any alleviation or prevention of an undesirable symptom (e.g., symptoms related to disease, sensitivity to environmental or factors, normal aging, and the like) would be desirable. Thus, for the purposes of this Application, the terms "treatment", "therapeutic use", or "medicinal use" used herein shall refer to any and all uses of the claimed compositions which remedy a disease state or symptoms, or otherwise prevent, hinder, retard, or reverse the progression of disease or other undesirable symptoms in any way whatsoever.

By the term "therapeutically effective amount" or grammatical equivalents herein refers to an amount of the preparation that is sufficient to regulate, either by stimulation or suppression, the systemic immune response of an individual. This amount may be different for different individuals, different tumor types and different cytokine preparations. An appropriate dosage of transduced cells, or derivatives thereof, may be determined by any of several well established methodologies. For instance, animal studies are commonly used to determine the maximal tolerable dose, or MTD, of bioactive agent per kilogram weight. In general, at least one of the animal species tested is mammalian. Those skilled in the art regularly extrapolate doses for efficacy and avoiding toxicity to other species, including human. Before human studies of efficacy are undertaken, Phase I clinical studies in normal subjects help establish safe doses. Alternatively, initial toxicity studies may involve individuals that are at the terminal stages of the disease progression.

By the term "rejection" or grammatical equivalents herein is meant a systemic immune response that does not allow the establishment of new tumor growth.

By the term "challenge" or grammatical equivalents herein is meant a subsequent introduction of tumor cells to an individual. Thus a "challenge dose 5 days post vaccination" means that on the fifth day after vaccination with tumor cells expressing cytokines or irradiated tumor cells, or both, a dose of unmodified tumor cells was administered. "Challenge tumor" means the tumor resulting from such challenge.

By the term "days to sacrifice" or grammatical equivalents herein, is meant that period of time before mice were sacrificed. Generally, mice were sacrificed when challenge tumors reached 2–3 centimeters in longest diameter, or if severe ulceration or bleeding developed.

By the term "irradiated cells" or "inactivated cells" or grammatical equivalents herein is meant cells inactivated by rendering them proliferation incompetent by irradiation. This treatment results in cells which are unable to undergo mitosis, but still retain the capability to express proteins such as cytokines. Typically a minimum dose of about 3500 rads is sufficient, although doses up to about 30,000 rads are acceptable. It is understood that irradiation is but one way to inactivate the cells, and that other methods of inactivation which result in cells incapable of cell division but that retain the ability to express cytokines are included in the present invention (i.e., treatment with mitomycin C and conceptually analogous agents).

By the term "individual" or grammatical equivalents herein is meant any one individual mammal.

The present invention relates to a method of regulating the immune response of an individual to target antigens by administering a mixture of the target antigen or antigens and a cytokine, or cytokines, in such a manner that the immune system of the individual is either stimulated or suppressed. In either case, the present invention provides a means of controlling the activity of the cytokines with the result that they provide an unusual protective or therapeutic effect.

In one embodiment of the present invention, the target antigen and one or more cytokines, adhesion or accessory molecules or combinations thereof, are administered to an individual in a chemical composition which provides for transfer or release of the cytokines, adhesion or accessory molecules or combinations thereof, in direct proximity or in combination with the target antigen. The two components need not be administered in the same vehicle. If they are administered in two separate vehicles, they must be administered sufficiently closely, both in time and by route of administration, that they are encountered essentially simultaneously by the individual's immune system. That is, the cytokines, adhesion or accessory molecules or combinations thereof, can be co-administered with the target antigen in any manner which provides transfer or delivery of the cytokine in the context of the target antigen in relation to which the immune response is to be regulated. For example, this can be accomplished by using slow or sustained release delivery systems, or direct injection. As a result of this co-administration, the nonspecific cytokine has the specific effect of amplifying or altering the specific immune response to the target antigen. The emphasis is on local interaction of the cytokine and the target antigen to mimic the physiological occurrence of simultaneous presentation of cytokine and antigen, to maximize efficacy and minimize toxicity.

In a preferred embodiment, cells which express the target antigen, such as tumor cells, are themselves genetically engineered to express the cytokines to be administered. The resulting modified tumor cells presents to the host immune system not only the antigen against which an immune response is sought, but also the cytokines, adhesion or accessory molecules or combinations thereof, whose expression determines the type and extent of the resulting immune response. Alternatively, cells that naturally express the target antigen and the cytokines can be used. The resulting cells, which express both the target antigen and the cytokines, can be used as a vaccine, to protect against future tumor development or as a delivery vehicle to result in the reversal of previously existing tumors. Conversely, a target antigen against which a decreased immune response is sought can be used in conjunction with the appropriate cytokine mixture.

In one embodiment, the individual's systemic immune response is increased or enhanced beyond that which would occur in the absence of the co-administered molecules. The systemic response is sufficient for the individual to mount an immune response against the target antigen, such as the tumor cells, and may cause the tumor cell to be rejected by the individual.

In another embodiment, the individual's systemic immune response is reduced or suppressed, either partially or completely, to such an extent that the target antigen, such as antigens on transplanted cells or tissue, or cells of the individual incorrectly recognized as foreign, is not rejected by the individual, or is rejected to a lesser extent than would occur if the present method were not used.

In one embodiment of the present invention, the target antigen can be a tumor cell, a tumor cell antigen, an infectious agent or other foreign agent against which an enhanced immune response is desired. For example, any antigen implicated in the progression of a chronic and life threatening infection, such as the AIDS virus or a secondary infection associated with AIDS, or other bacterial, fungal, viral, parasitic and protozoal antigens, may be utilized in the present invention.

In a preferred embodiment, the target antigen is a tumor cell. One preferred embodiment utilizes melanoma cells, and another embodiment utilizes carcinoma cells. However, other tumor cells such as, but not limited to, breast cancer cells, leukemia cells, cancerous polyps or preneoplastic lesions, or cells engineered to express an oncogene (e.g. ras, p53) may also be used. The modified cells may be live or irradiated cells, or cells inactivated in other ways. Furthermore, the tumor cells used as the target antigen and expressing cytokines can be either an unselected population of cells or specific clones of modified cells.

In a preferred embodiment, tumor cells are modified to express the cytokines IL-2 and GM-CSF. This combination is particularly desirable since it results in the long term systemic immune protection against subsequent challenge with wild type tumor cells.

In one embodiment of the present invention, tumor cells expressing the target antigen and the cytokines are irradiated before administration to an individual. The resulting nonviable tumor cells may be used to regulate the immune response of the individual. The administration of such irradiated cytokine producing tumor cells has been shown to be useful in inhibiting the establishment of tumors of the same type, presumably through a vaccine-like mechanism. This procedure has particular importance since the introduction of live tumor-producing cancer cells to an individual is undesirable. This has additional significance since primary tumor explants likely contain non-neoplastic elements as well, irradiation of the tumor samples prior to vaccination will also prevent the possibility of autonomous growth of non-neoplastic cells induced by autocrine synthesis of their own growth factors.

In a preferred embodiment, the irradiated tumor cells used to regulate the immune response of an individual are capable of expressing GM-CSF, IL-4, IL-6, CD2 or ICAM, or a combination thereof.

In the most preferred embodiment, the irradiated tumor cells used to regulate the immune response of an individual are capable of expressing GM-CSF.

In one embodiment, the administration of the combination of target antigen and cytokines can be used to reverse established tumors. This may be accomplished by taking tumor cells from an individual with a pre-existing tumor and modifying these tumor cells to express cytokines. Upon subsequent re-introduction of the modified cells into the individual, a systemic immune response capable of reversing the pre-existing tumor is produced. Alternatively, tumor cells of the type of the pre-existing cancer may be obtained from other sources. The identification of the cytokines to be expressed will depend on the type of tumor, and other factors.

In a preferred embodiment of the present invention, the tumor cells express IL-2 and GM-CSF, and a third cytokine from the group TNF-α, IL-4, CD2 and ICAM.

In the most preferred embodiment, the tumor cells express IL-2, GM-CSF and/or TNF-α.

In another embodiment, the modified tumor cells used to reverse established tumors are irradiated prior to administration to the individual.

In a preferred embodiment, the irradiated tumor cells used to reverse an established tumor are capable of expressing GM-CSF.

In one embodiment of the present invention, a vector such as the retroviral MFG vector herein described may be used to genetically alter the vaccinating cells. The MFG vector has particular utility since its use makes it feasible, for the first time, to rapidly screen a large number of potential immunomodulators for their effects on the generation of systemic immunity and to assess the activity of complex combinations of molecules. The MFG vector's combination of high titer and high gene expression obviates the need for selection of transduced cells among the bulk target population. This minimizes the time required for culturing primary tumor cells prior to vaccination, and maximizing the antigenic heterogeneity represented in the vaccinating inoculum.

Figure 1B:
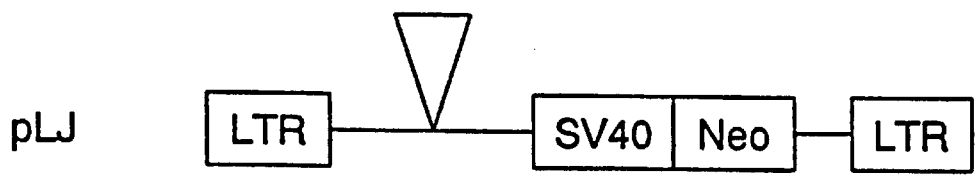
Figure 1C:
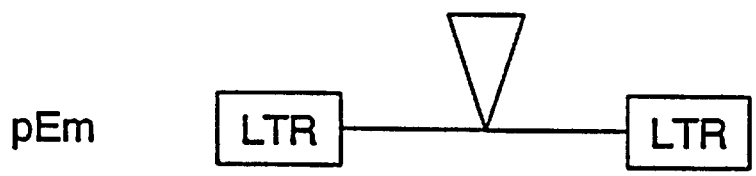
Figure 1D:
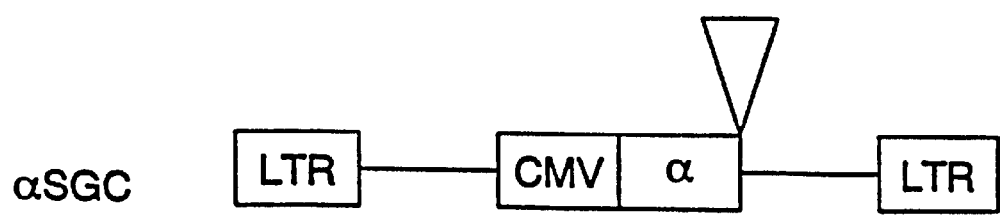

Other retroviral vectors will find use in the present invention. For example, pLJ, pEm, and α-SGC may be used. pLJ, previously described in (20), is capable of expressing two types of genes: the gene of interest and a dominant selectable marker gene, such as the neo gene. The structure of pLJ is represented in FIG. 1B. pEm is a simple vector where the gene of interest replaces the gag, pol and env coding sequences of the wild-type virus. The gene of interest is the only gene expressed. The structure of pEm is represented in FIG. 1C. The vector α-SGC utilizes transcriptional promoter sequences from the α-globin gene to regulate expression of the gene of interest. The structure of α-SGC is represented in FIG. 1D.

On Oct. 3, 1991, Applicants have deposited with the American Type Culture Collection, Rockville, Md. USA (ATCC) the plasmid MFG with the factor VIII insertion, described herein ATCC accession no. 68726, plasmid MFG with the tPA insertion, given ATCC accession no. 68727, the plasmid α-SGC, described herein, with the factor VIII insertion, given ATCC accession no. 68728, and plasmid α-SGC with the tPA insertion, given ATCC accession no. 68729. On Oct. 9, 1991, Applicants have deposited with the ATCC the plasmid MFG, described herein, given ATCC accession no. 68754, and plasmid α-SGC, described herein and given ATCC accession no. 68755. These deposits were made under the provisions of the Budapest Treaty on the International Recognition of the Deposit of Microorganisms for the purposes of patent procedure and the Regulations thereunder (Budapest Treaty). This assures maintenance of a viable culture for 30 years from the date of deposit. The organisms will be made available by the ATCC under the terms of the Budapest Treaty, and subject to an agreement between Applicants and ATCC which assures unrestricted availability upon issuance of the pertinent U.S. patent. Availability of the deposited strains is not be construed as a license to practice the invention in contravention of the rights granted under the authority of any government in accordance with its patent laws.

One of ordinary skill will realize that the above vectors may be subtly altered in a manner such that the operative features vis-a-vis transduction efficacy are substantially maintained. As such, the present invention also contemplates the use of any and all operative (transfection competent) derivatives of the above retroviral constructs to deliver genes encoding immunomodulatory agents to cells. For example, the vector MFG-S comprises three point mutations in the MFG vector which theoretically improve the safety of the vector (although there is no evidence that MFG is unsafe) while retaining substantially identical transfection efficiency. Specifically, MFG-S has an A to T change at nucleotide 1256, a C to T mutation at nucleotide 1478, and a T to an A at nucleotide 1273.

It follows from the results herein that a variety of hormones, antigens, and cytokines will find use in the present invention. For example, cytokines, antigens, or hormones of other mammals with substantial homology to the human forms of the cytokines, antigens, and hormones, will be useful in the invention when demonstrated to exhibit similar activity on the immune system.

Thus, the method of the present invention can include treatment with antigens, hormones, and cytokines, adhesion or accessory molecules or combinations thereof, combined with other systemic therapy such as chemotherapy, radiation treatments and other biological response modifiers.

The method of the present invention can also be used to regulate an individual's systemic immune response to a variety of antigens. In one embodiment, the present invention may be used to treat chronic and life threatening conditions, such as infection with the AIDS virus, as well as the secondary infections associated with AIDS. Other embodiments embrace the treatment of other bacterial, fungal, viral, parasitic, and protozoal infections described in "Principles and Practice of Infectious Disease", Mandell et al., eds. 1990, Churchill Livingstone, Inc., New York, N.Y.) herein incorporated by reference.

In a preferred embodiment, treatment and prevention of HIV-related conditions is achieved. For example, in the case of the human immunodeficiency virus (HIV), Simian immunodeficiency virus (SIV) there are at least six known target antigens (21, 22, 23) against which an immune response can be enhanced using the present invention. An appropriate host cell expressing the HIV target antigen can be modified to express one or more cytokines and administered to an uninfected individual, to serve as a vaccine and elicit an enhanced immune response to confer the ability to resist subsequent infection by the AIDS virus.

Alternatively, the antigen and the cytokines may be administered without a host cell. Furthermore, co-administration of the target antigen and cytokines can be given to an HIV positive individual, in order to limit the existing infection or reverse it.

Having described the particular methods employed in the present invention for the regulation of systemic immune responses to target antigens, and detailing how these methods may be utilized, and showing the successful regulation of systemic immune responses, the present disclosure is sufficient to enable one skilled in the art to use this knowledge to produce the end results by equivalent means using generally available techniques.

The following examples serve to more fully describe the manner of making and using the above-described invention, as well as to set forth the best modes contemplated for carrying out various aspects of the invention. It is understood that these examples in no way serve to limit the true scope of this invention, but rather are presented for illustrative purposes.

VII. EXAMPLES

7.1. Generation of Recombinant Retroviral Genomes Encoding Cytokines

Construction of the retroviral vectors employs standard ligation and restriction techniques which are well understood in the art. A variety of retroviral vectors containing a gene or genes encoding a cytokine of interest were used.

MFG. This vector is described in co-pending U.S. Ser. No. 07/607,252 entitled "Genetic Modification of Endothelial Cells", filed Oct. 31, 1990, abandoned U.S. Ser. No. 07/786,015; abandoned "Retroviral Vectors Useful in Gene Therapy", filed Oct. 31, 1991, and PCT/US91/08121, filed Oct. 31, 1991, the teachings of which are incorporated herein by reference. They are also described below with particular reference to the incorporation and expression of genes encoding cytokines. Furthermore, several MFG vectors have been deposited with the TCC as described above.

The MFG vector is similar to the pEm vector, described below and depicted in FIG. 1, but contains 1038 base pairs of the gag sequence for MoMuLV, to increase the encapsidation of recombinant genomes in the packaging cells lines, and 350 base pairs derived from MOV-9 which contains the splice acceptor sequence and transcriptional start. An 18 base pair oligonucleotide containing NcoI and BamHI sites directly follows the MOV-9 sequence and allows for the convenient insertion of genes with compatible sites. In each case, the coding region of the gene was introduced into the backbone of the MFG vector at the NcoI site and BamHI site. In each case, the ATG initiator methionine codon was subcloned in frame into the Nco I site and little, if any, sequence beyond the stop codon was included, in order to avoid destabilizing the product and introducing cryptic sites. As a result, the ATG of the insert was present in the vector at the site at which the wild-type virus ATG occurs. Thus the splice was essentially the same as occurs in Moloney Murine Leukemia virus and the virus worked very well. The MoMuLV LTR controls transcription and the resulting mRNA contains the authentic 5' untranslated region of the native gag transcript followed directly by the open reading frame of the inserted gene. In this vector, Moloney murine leukemia virus (Mo-MuLV) long terminal repeat sequences were used to generate both a full length viral RNA (for encapsidation into virus particles), and a subgenomic mRNA (analogous to the Mo-MuLV env mRNA) which is responsible for the expression of inserted sequences. The vector retained both sequences in the viral gag region shown to improve the encapsidation of viral RNA (24) and the normal 5' and 3' splice sites necessary for the generation of the env mRNA. All oligonucleotide junctions were sequenced using the dideoxy termination method (25) and T7 DNA polymerase (Sequenase 2). The structure of MFG is represented in FIG. 1A. As can be seen, the virus in marker-free in that it does not comprise a dominant selectable marker (although one may optionally be inserted), and, given the high levels of transfection efficiency and expression inherent in the structure of the vector, transduction with MFG derivatives generally does not involve or require a lengthy selection step.

MFG vectors containing genes for the following proteins were constructed: murine IL-2, GM-CSF, IL-4, IL-5, γ-IFN, IL-6, ICAM, CD2, TNF-α, and IL-1-RA (interleukin-1-receptor antagonist). In addition, human sequences encoding TNF-α, GM-CSF and IL-2 were constructed (See Table 1). It is also possible to make MFG vectors containing a gene encoding one or more of the following: VCAM, ELAM, macrophage inflammatory protein, heat shock proteins (e.g. hsp60), M-CSF, G-CSF, IL-1, IL-3, IL-7, IL-10, TGF-β, B7, MIP-2, MIP-1 α and MIP-1 β.

Precise cDNA sequences subcloned into MFG were as follows: murine IL-2 (26) base pairs 49–564; murine IL-4 (27) base paris 56–479; murine IL-5 (28) base pairs 44–462; murine GM-CSF (29) base pairs 70–561; murine ICAM-1 (30) base pairs 30–1657; murine CD2 (31) base pairs 48–1079; murine IL-1 receptor antagonist (32) base pairs 16–563; human TNF-60 (33) base pairs 86–788.

7.2. Cytokine Assays

Cytokines secreted by the infected, unselected B16 populations were assayed 48 hours after plating $1 \times 10^6$ cells in 10 cm dishes containing 10 mls. of medium. IL-1-RA secretion was measured from infected, unselected 3T3 cells 24 hours after plating $5 \times 10^6$ cells in a 10 cm dish containing 10 mls of medium. Cytokines were assayed as follows: murine IL-2 using CTLL cells (34) and ELISA (Collaborative Biomedical); murine IL-4 using CT4R cells (35) and ELISA (Endogen); murine IL-5 using an ELISA (Endogen); murine IL-6 using T1165 cells (41) and ELISA (Endogen); murine GM-CSF using FDCP-1 cells (37) and ELISA (Endogen); murine γ-IFN using vesicular stomatitis viral inhibition (38) and ELISA (Genzyme); human TNF-α using L929 cells (39) and ELISA (R&D Systems); murine IL-1-RA using $^{125}$I-IL1β binding inhibition (40).

Expression of murine ICAM-1 and CD2 in B16 target cells was determined with standard procedures (41) on an EPICS-C FACS analyzer (Coulter) using antibodies YN1/1.47 (42) and RM2/1 respectively.

7.3. Production of B16 Melanoma Cells Containing Cytokine-encoding Sequences The above vector constructs were introduced by standard methods into the packaging cell lines known as Psi CRIP and Psi CRE (43). These cell lines have been shown to be useful to isolate clones that stably produce high titres of recombinant retroviruses with amphotropic and ecotropic host ranges, respectively. Psi CRIP packaging lines with amphotropic host range were generated by both transfection and electroporation with only small differences in efficiency. Calcium phosphate DNA coprecipitations were performed (44) using 20 μg of vector and 1 μg of pSV2NEO (45). Electroporations were performed after linearizing 40 μg of vector and 8 μg of pSV2NEO using the Gene Pulser electroporator (Bio-Rad). Conditions were 190 V and 960 μF. Producers were placed into selection in G418 (GIBCO) at 1 mg/ml 36 hours after introduction of the DNA. Both clones and populations of producers were generated.

Viral titres were determined by Southern blot analysis (46) following infection (47) of B16 or 3T3 cells in medium containing 8 μg polybrene per ml. Ten μg of infected target cell DNA as well as control DNA spiked with appropriate copy number standards were digested with Nhe I (an LTR cutter), resolved by electrophoresis in 1% agarose gels, and analyzed by the method of Southern using standard procedures (48). Blots were probed with the appropriate sequences which had been labeled to high specific activity with [$^{32}$P]dCTP by the random primer method (49). Probes used were all full-length cDNAs except for murine IL-2 which was the SacI/RsaI fragment (base pairs 221–564). A titre of one copy per cell is approximately equivalent to $1 \times 10^6$ retroviral particles per cell.

During the course of generating these products, we observed that cross-infection of packaging lines (CRE to CRIP or CRIP to CRE) with MFG vectors sometimes led to the mobilization of packaging function as determined by a sensitive his D mobilization assay (43). Such cross-infection should thus be avoided. No mobilization of packaging function with producers generated by direct transfection or electroporation has been observed.

Viral titres and expression levels are shown in the Table below.

TABLE 1

MFG Vector Constructs

| Construct | Titre (Ampho) | Expression |
|---|---|---|
| MFG mu IL-2 | 1.0 copy | 5000 U/ml |
| MFG mu IL-4 | 0.25 copy | 15 ng/ml |
| MFG mu IL-5 | 2.0 copy | 250 ng/ml |
| MFG mu IL-6 | 0.5 copy | 400 ng/ml |
| MFG mu GM-CSF | 2.0 copy | 300 ng/ml |
| MFG mu γ-IFN | 0.1 copy | 20 ng/ml |
| MFG mu ICAM | 0.5 copy | +FACS |
| MFG mu CD2 | 0.5 copy | +FACS |
| MFG mu IL1RA | 1.0 copy | 30 ng/ml |
| MFG hu IL-2 | 1.0 copy | 100 ng/ml |
| MFG hu GM-CSF | 1.0 copy | 500 ng/ml |
| MFG hu TNF | 0.5 copy | 400 ng/ml |

The B16 melanoma tumor model (50) was chosen for initial studies. Human melanoma has been shown to be sensitive to a variety of immunotherapies (51, 52). To examine whether any of the gene products listed in Table 1 influenced the growth of B16 cells in vitro or in vivo, cells were exposed to viral supernatants and the transduced cells were characterized for their efficiency of infection and secretion of gene product. Table 1 shows the approximate efficiency of infection with each virus for the B16 melanoma cell line (a titer of one copy per cell corresponds to a titer of approximately $10^6$ infectious particles) and the corresponding level of secreted gene product.

With the exception of the MFG γ-IFN construct, which transmitted at approximately 0.1 copies/cell, most of the viruses were capable of transducing a majority of tumor cells. γ-IFN secreting cells grew more slowly than non-infected cells and adopted a flattened morphology relative to their wild type counterparts. In contrast, none of the other transduced cells displayed any altered in vitro growth characteristics. Both populations and specific clones of virus producing cells were used in these studies.

7.4. Vaccinations

Tumor cells were trypsinized, washed once in medium containing serum, and then twice in Hanks Balanced Saline Solution (GIBCO) prior to injection. Trypan blue resistant cells were suspended to the appropriate concentrations and injected in a volume of 0.5 cc HBSS. Vaccinations were administered subcutaneously in the abdomen and tumor challenges were injected in the dorsal midline of the back after anesthetizing the mice with Metaphane (Pitman-Moore). Mice were examined at 2–3 day intervals and the time to development of palpable tumor recorded. Animals were sacrificed when tumors reached 2–3 cm in diameter or if severe ulceration or bleeding developed. For antibody depletion experiments, mice were vaccinated in the right hind leg (volume 0.1 cc) and challenged in the left hind leg (volume 0.1 cc). For establishment of pulmonary metastases, cells were injected in the tail vein in a volume of 0.2 cc. Animals used were 6–12 week C57B⅙ females (Jackson Labs) for B16, Lewis Lung, and WP-4 experiments, and 6–12 week Balb/c females (Jackson Labs) for CT-26, RENCA, and CMS-5 studies.

When irradiated vaccines were employed, tumor cells (after suspension in HBSS) received 3500 rads from a Cesium-137 source discharging 124 rads/min.

7.5. Histology

Tissues for histologic examination were fixed in 10% neutral buffered formalin, processed to paraffin embedment, and stained with hematoxylin and eosin. Tissues for immunoperoxidase staining were snap frozen in liquid $N_2$, frozen sections were prepared, fixed in acetone for 10 minutes, and stored at $-20°$ C. Frozen sections were stained with primary antibodies, followed by anti-IgG antibodies (species specific), and then the antigen-antibody complexes visualized with avidin-biotin-peroxidase complexes (Vectastain, Vector Labs) and diaminobenzidine. Primary antibodies used were 500A2 (hamster anti-CD3), GK 1.5 (rat anti-CD4), and GK2.43 (rat anti-CD8).

7.6. Vaccination Studies with Live Transduced Tumor Cells

To directly assess the effect of the cytokine upon the tumorigenicity of B16 cells, either unmodified (wild type) B16 melanoma cells or the transduced modified cells were inoculated subcutaneously into C57B⅙ mice, their syngeneic host, and the mice were examined every few days for tumor formation. Typically, a vaccinating dose was $5 \times 10^5$ infected B16 cells.

Surprisingly, only tumor cells secreting IL-2 did not form tumors. All of the other nine cytokines tested resulted in tumor formation. Modest delays in tumor formation were associated with expression of IL-4, IL-6, γ-INF, and TNF-α. Several cytokines produced distinctive systemic syndromes, presumably as a consequence of the progressively increasing number of cells. GM-CSF transduced cells induced a fatal toxicity manifested by profound leukocytosis (polymorphonuclear leukocytes, monocytes, and eosinophils), hepatosplenomegaly, and pulmonary hemorrhage, IL-5 expressing cells showed a striking peripheral eosinophilia and splenomegaly. IL-6 expressing cells caused hepatosplenomegaly and death. TNF-α expressing cells induced wasting, shivering, and death.

7.7. Systemic Antitumor Immunity Generated by Cytokine-Transduced Tumor Cells The rejection of IL-2 transduced cells made it possible to examine their potential to generate systemic immunity. Mice were first inoculated with IL-2 expressing B16 melanoma cells, and subsequently challenged over the course of one month, with unmodified B16 cells. Typically, both the initial and challenge dose were $5 \times 10^5$ live cells, cells which had been harvested from culture dishes and then extensively washed. Cells were injected subcutaneously in a volume of about 0.5 cc (in Hanks Buffered Saline (HBS)). Groups of 5 mice were then challenged at a site different from that at which the vaccine was administered. A time course analysis was carried out by challenging groups of 5 animals every 3–4 days, beginning 3 days after the vaccine was administered and continuing to challenge the animals until a month after the vaccination.

The results demonstrated that IL-2 possessed a minimal ability to induce systemic protection, as measured by the ability of the unmodified tumor challenge to be rejected. In a typical experiment, most mice succumbed to the challenge tumor by 40 days after its inoculation. This is in direct contrast to the results of Fearon et al. (8), since all animals succumbed to this challenge, regardless of the time of challenge, with only an occasional delay in tumor formation, FIG. 2A. Assessment of the effects of the infected B16 cells was done through ascertaining when natural death or humane killing of the mice occurred.

7.8. Systemic Antitumor Immunity Generated by Multiple Cytokine-Transduced Cells As a result of the demonstration that tumor cells transduced with IL-2 alone may be effectively rejected, combinations of cytokines were tested. For this analysis, populations of B16 cells expressing both IL-2 and a second gene product were generated through the superinfection of IL-2 transduced cells. Animals were vaccinated with the doubly infected cells and then challenged with non-transduced cells after 7 to 14 days.

Typically, both the initial and challenge doses were $5 \times 10^5$ live cells, cells which had been harvested from culture dishes and then extensively washed. Cells were injected subcutaneously in a volume of roughly 0.5 cc of HBS.

B16 melanoma cells were modified to express IL-2 plus one of the following: GM-CSF, IL-4, γ-IFN, ICAM, CD2, ILL-RA, IL-6, or TNF-α.

The results shown in FIG. 2B, indicate that cells expressing both IL-2 and GM-CSF generate potent systemic immunity, with a majority of the mice surviving tumor challenge long term. For example, mice often survived as long as 120 days, at which time the mice were sacrificed. In total, 50 or 60 mice have been vaccinated with this combination, and the result show that mice were protected from challenge doses ranging from $10^5$ unmodified cells (essentially 70% of the animals were protected) to $5 \times 10^6$ unmodified cells (which resulted in lesser, but still significant protection). This result is particularly surprising in light of the fact that tumor cells infected with GM-CSF alone grew progressively in the host, and, in fact, the host succumbed to the toxicity of GM-CSF secreted systemically. A small degree of protection was observed with several other combinations. TNF-α and IL-4 had a very slight effect in combination with IL-2. IL-6 also showed slight activity when used in combination with IL-2. Under the conditions used, T-IFN, ICAM, CD2 and IL1 receptor antagonists were inactive. Assessment of the effects of the infected B16 cells was done through ascertaining when natural death or humane killing of the mice occurred.

In a further set of experiments, the ability of a third cytokine (in addition to IL-2 and GM-CSF) to affect the ability of that combination to protect against wild type challenge was also assessed. Thus, B16 melanoma cells expressing IL-2, GM-CSF plus either γ-IFN, IL-4, or both, were constructed.

Preliminary results suggest that the addition of IL-4 to IL-2 with GM-CSF improves the efficacy of this approach. See FIG. 2C. Perhaps more intriguing is that the addition of γ-IFN to IL-2 with GM-CSF compromises the ability of the ladder combination to function as an effective vaccine.

These data suggests that the various combinations of cytokines can both enhance as well as attenuate the magnitude of the immune response.

7.9. Vaccination Studies With Irradiated Cells

7.9.1. Immunogenicity of Non-Transduced, Irradiated Cells

The fact that cells expressing both IL-2 and GM-CSF, but not IL-2 alone, conferred systemic protection upon vaccinated hosts, and that cells secreting GM-CSF alone actually grew progressively, suggested the possibility that the IL-2 might be functioning primarily to mediate rejection of the vaccinating cells.

Thus, an important control was to assess the vaccination potential of non-transduced irradiated cells, since many previous studies have shown that irradiated tumor cells can possess significant vaccination activity. (16, 17, 18, 19). Irradiation and vaccination were done as outlined above. The data in FIG. 3C indicates that non-transduced irradiated B16 cells elicited only minimal effects upon the growth of challenge cells at the vaccine and challenge doses tested.

However, a number of mouse tumor cell lines previously used to identify the anti-tumor activity of specific cytokines are inherently immunogenic, as revealed by studies involving vaccination with irradiated, non-transduced cells. Furthermore, irradiated cells alone are able to confer systemic immunity at levels comparable to those induced by live transduced cells. For these experiments, several tumor models which had been used previously by other investigators to identify cytokines possessing activity in tumor rejection or tumor challenge assays were used. These tumors included: (i) CT26, a colon carcinoma derived cell line (53), used in studies which identified the activity of IL-2 (8); (ii) CMS-5, a fibrosarcoma derived cell line (54), used to identify the activity of IL-2 (9) and γ-IFN (4); (iii) RENCA, a renal cell carcinoma derived cell line (55), used to identify the activity of IL-4 (15); and (iv) WP-4, a fibrosarcoma derived cell line (2), used to identify the activity of TNF-α (2). For these initial studies, the vaccine and challenge doses were comparable to those used previously in the cytokine gene transfer studies. The results of tumor challenge assays in which mice vaccinated with irradiated cells were challenged with tumor cells 7–14 days later are shown in FIG. 7.

Surprisingly, in each case, the irradiated cells possessed potent vaccination activity, comparable to that reported previously with live cells expressing the various cytokines tested above. In contrast, as shown earlier (FIG. 3C), irradiated B16 cells induced little if any systemic immunity. This has particular significance since it suggests that previous work may be misleading. Many of the tumor cells used in previous studies could have been inherently immunogenic, but the lethality of the live tumor cells masks such characteristics.

The expression of a cytokine may merely mediate the death of the live tumor cells, thus allowing the natural immunogenicity to be expressed. In contrast, the systemic immune responses of the present invention are due to a real interaction of the immune system and the simultaneous presentation of cytokine and antigen.

7.9.2. Vaccination With Irradiated, Transduced B16 Cells

As shown above, irradiation of B16 cells expressing both IL-2 and GM-CSF did not abrogate either their secretion of cytokines in vitro or their vaccination activity in vivo (data not shown). Based on this result, irradiated B16 cells expressing GM-CSF alone were used to vaccinate mice, and subsequently challenged 7 to 14 days later. Cells were irradiated using 3500 rads. Typically the irradiated cells were dosed at $5 \times 10^5$, with subsequent challenge with the same dose of live cells. As shown in FIG. 3A, such a vaccination led to potent anti-tumor immunity, with most of the mice surviving their tumor challenge. When non-radiated cells were used as a vaccine, 1 out of 19 animals was ultimately protected; when irradiated cells were used, 16 out of 20 mice were protected. No mice demonstrated the toxicity observed in mice injected with live GM-CSF expressing cells and we were unable to detect circulating GM-CSF in the sera of vaccinated mice using an ELISA sensitive to 10 pg/ml. The systemic immunity was also shown to be long lasting, in that most of the mice vaccinated with irradiated cells which expressed GM-CSF and subsequently challenged with non-transduced cells two months after vaccination remained tumor free (data not shown).

The systemic immunity was also specific, in that GM-CSF expressing B16 cells did not protect mice from a challenge by Lewis Lung carcinoma cells, (56), another tumor of C57Bl/6 origin, and GM-CSF expressing Lewis Lung carcinoma cells did not protect mice from a challenge of non-transduced B16 cells (data not shown).

The efficiency of the irradiated transduced cells as a vaccine was apparent over a wide range of GM-CSF concentrations in that infected cells could be admixed with a one hundred fold excess of non-transduced cells, with little compromise in systemic immunity, FIG. 3B. This result may reflect the relatively high levels of GM-CSF expression afforded by the MFG vector. In contrast, protection was highly sensitive to the total inoculum of vaccinating cells, as activity was severely compromised with the use of ten fold fewer vaccinating cells. FIG. 3B.

In addition to conferring potent protection against challenge with non-transduced cells, irradiated B16 cells expressing GM-CSF were also more capable of mediating the rejection of pre-established tumors than were irradiated cells alone, FIG. 3C. Similar results were also obtained in studies in which established metastases were generated through the intravenous injection of non-transduced cells (data not shown).

Surprisingly, the localized destruction of vaccinating cells does not always lead to systemic immunity, as evidenced by the B16 results. While live IL-2 expressing B16 cells were rejected by the syngeneic host, this vaccination did not generate protection against subsequent challenge of non-transduced B16 cells. Similarly, vaccination with non-transduced irradiated B16 cells also failed to induce systemic protection. The generation of systemic immunity in non- or poorly immunogenic tumor models may thus require qualitatively different mechanisms than those responsible for inducing this immunity in more immunogenic tumor models.

Consistent with this hypothesis is that a screen of many gene products for anti-tumor activity in the B16 model, including all of the molecules identified in other systems as able to augment such immunity, showed that a previously unidentified cytokine, GM-CSF, is quite potent.

Demonstration of the advantage of GM-CSF transduction even in tumor models that are somewhat immunogenic further suggests the relative potency of GM-CSF expression in comparison to other means of revealing tumor immunogenicity.

Finally, to determine whether irradiated cells expressing other gene products might also confer systemic immunity upon vaccinated hosts, a survey of each of the cell populations expressing different gene products (after irradiation) for vaccination activity was done. B16 cells expressing IL-1-RA, IL-2, IL-4, IL-5, IL-6, GM-CSF, γ-IFN, TNF, ICAM and CD2 were constructed as described previously. Vaccination and challenge doses and methods were done as described previously.

The results, shown in FIG. 4, show that B16 cells expressing GM-CSF prior to irradiation appeared to be the most potent, with IL-4 and IL-G modified cells showing slightly reduced activity.

7.9.3. Vaccination with Irradiated, GM-CSF Expressing Cells in Other Murine Tumor Models Because the significant vaccination activity of the irradiated cells of the other murine tumor models alone precluded examination of the activity of GM-CSF expressing cells, either the challenge or vaccine dose of a number of the tumors examined above were manipulated, in the hopes of establishing conditions where the relative efficiency of non-transduced irradiated and irradiated cells expressing GM-CSF could be evaluated. These conditions were the same as the ones employed relating to FIG. 3B. These conditions made possible the comparison of non-transduced irradiated and GM-CSF expressing irradiated cells shown in FIG. 8. While the relative efficacy of GM-CSF expressing cells was somewhat variable from line to line, GM-CSF expressing cells in all cases were more efficacious than irradiated cells alone in eliciting systemic immunity.

As outlined above, included in this analysis was a study of the Lewis Lung carcinoma cell line (56), a tumor not previously employed in cytokine gene transfer studies. While a representative experiment illustrating the efficacy of GM-CSF transduction is shown, the precise dose which demonstrates this effect has been somewhat variable.

However, the results show that Lewis Lung carcinoma cells which express GM-CSF prior to irradiation show a specific systemic immunity, in that mice were protected from a subsequent challenge with unmodified Lewis Lung carcinoma cells but not from challenge with unmodified B16 melanoma cells (data not shown).

The WP-4 cell line was not included in this experiment, since even large challenge doses were eventually rejected after vaccination with non-transduced cells (data not shown).

7.10. Reversal of Pre-Existing Tumors Using Cytokine-Transduced Tumor Cells

The ability of B16 melanoma cells expressing mixtures of cytokines to affect growth of a pre-existing tumor was tested. All experiments used mice subcutaneously injected with unmodified B16 cells on day 1. By day 7, tumors were microscopically established. On day 7, B16 melanoma cells expressing various cytokines were injected at a different subcutaneous site. Typically, both the initial and challenge doses were $5 \times 10^5$ live cells, cells which had been harvested from culture dishes and then washed extensively. Cells were injected subcutaneously in a volume of roughly 0.5 cc of HBS.

B16 melanoma cells were modified to express the following combinations of cytokines: IL-2 and GM-CSF; IL-2, GM-CSF and TNF-α; IL-2, GM-CSF and IL-4; IL-2, GM-CSF and IL-6; IL-2, GM-CSF and ICAM; IL-2, GM-CSF and CD2; and IL-2, GM-CSF and IL-1-RA. The results of these studies are shown in FIG. 9.

The experiments showed that if mice with pre-existing tumors were treated with modified B16 cells containing IL-2 and GM-CSF, there was a slight prolongation of the animal's life relative to controls. No mice were cured. Conversely, treatment with the IL-2, GM-CSF, TNF-α combination resulted in the apparent cure of 3 out of 5 mice, as evidenced by survival in excess of 120 days. Two of the three mice survived a subsequent challenge of wild-type B16 cells. The addition of IL-4, ICAM or CD2, individually, to IL-2 and GM-CSF expressing cells resulted in a apparent cure of 1 out of 5 mice (the mice survived up to the end of the study, and displayed no overt signs of tumor-associated illness). If treatment with the modified IL-2, GM-CSF, and TNF-α cells began 3 days after the establishment of the tumor, more animals were apparently tumor free, and, in some groups, 10 out of 10 mice were apparently cured.

Reversal of established tumors was also shown using irradiated cells, as outlined in Example 9. As shown in FIG. 3C, irradiated B16 cells expressing GM-CSF were capable of mediating the rejection of pre-established tumors, while irradiated non-transduced cells were not, at least at the doses tested. FIG. 3C shows that the extent of protection was dependent upon both the dose of challenge cells and the time at which the therapy was initiated. Similar results were also obtained in studies in which established metastases were generated through the intravenous injection of non-transduced cells (data not shown),

7.11. Characteristics of the Immune Response Elicited by GM-CSF Expressing Tumor Cells The immune response elicited by vaccination with irradiated B16 melanoma cells expressing GM-CSF was characterized in a number of ways. Histological examination of the site of injection of irradiated GM-CSF expressing cells five to seven days after injection revealed an extensive local influx of immature, dividing monocytes, granulocytes (predominantly eosinophils), and activated lymphocytes (FIG. 5, panel A). Within one week after injection, the draining lymph mode had dramatically enlarged, showing paracortical hyperplasia and some germinal center formation (FIG. 5, panel C). In contrast, in mice vaccinated with non-transduced irradiated cells, only a mild influx of inflammatory cells was seen (FIG. 5, panel B), which consisted primarily of lymphocytes, and a comparatively smaller enlargement of the draining lymph node was observed (FIG. 5, panel D). At the challenge site of mice vaccinated with irradiated GM-CSF expressing cells (FIG. 5, panel E), a large number of eosinophils, monocytes, and lymphocytes were evident after five days, while only patches of lymphocytes were seen at the challenge site in mice vaccinated with irradiated cells (FIG. 5, panel F). Virtually no responding cells were observed in naive animals challenged with live B16 cells (FIG. 5, panel G).

To determine which cells were critical for systemic immunity, a series of mice were depleted of CD4+, CD8+, or natural killer cells by the administration of antibodies in vivo and subsequently vaccinated with irradiated GM-CSF expressing cells. Specifically, beginning one week prior to vaccination, mice were depleted of either CD4+ cells with Mab GK1.5 CD8+ cells with Mab 2.43, or NK cells with PK 136. The antibodies were partially purified by ammonium sulfate precipitation:delipidated ascites was mixed 1:1 with saturated ammonium sulfate and the precipitate was collected by centrifugation, dried, and resuspended in a volume of $dH_2O$ equivalent to the original volume of ascites. The antibody was dialyzed extensively against PBS and passed through a 0.45 μm filter. Antibody titre was tested by staining $1 \times 10^6$ splenocytes with serially diluted antibody and determining saturation by FACSCAN analysis. All preparations were titred beyond 1:2000. Antibodies were injected at a dose of 0.15 ml i.u. and 0.1 ml i.p. on day 1 of depletion, and 0.1 ml i.p. every week thereafter. Depletion of lymphocyte subsets was assessed on the day of vaccination (early depletions) on the day of wild type tumor challenge (early and late depletions), and weekly thereafter. Flow cytometric analysis of lymph node cells and splenocytes stained with 2.43 or GK1.5 followed by fluorescein isothiocyanate labeled goat antibody to rat IgG or with Pkl 36 followed by fluorescein isothiocyanate-labeled goat antibody to mouse IgG revealed that the depleted subset represented <0.5% of the total lymphocytes, with normal levels of the other subsets present. Both CD4+ and CD8+ T cells were required for effective vaccination, since depletion of either T cell subset prior to vaccination abrogated the development of systemic immunity, whereas depletion of NK cells had little or no effect (FIG. 6, panel A).

In addition, when various T cell subsets were depleted subsequent to immunization but prior to challenge, both CD4+ and CD8+ T cells were again found to be important (data not shown), thus indicating a role for both subsets at the effector as well as the priming phase of the response.

Finally, the generation of tumor specific CD8+ cytotoxic T cells in mice vaccinated with either non-transduced irradiated cells or irradiated cells expressing GM-CSF was examined. In this series of experiments, 14 days after vaccination with either irradiated GM-CSF transduced or non-transduced B16 cells, splenocytes were harvested and stimulated in vitro for 5 days with gamma-interferon treated B16 cells. CD8 blockable CTL activity was determined in a 4 hour $^{51}Cr$ release assay on gamma-interferon treated B16 targets at various effector:target ratios. Splenocytes from naive C57B⅙ and Balb/c mice served as controls. The data are shown in FIG. 6B, where the hollow square represents GM-CSF, the solid circle represents Allo, the hollow diamond represents naive and the solid triangle represents B16 irradiation.

While mice vaccinated with non-transduced cells possessed little detectable CD8+ blockable killing, the level of CD8 blockable killing was significantly enhanced in sample of cells isolated from mice vaccinated with GM-CSF expressing cells.

Previous studies had suggested that cytokine expressing tumor cells might enhance the generation of systemic anti-tumor immunity through the ability of cytokine expression to bypass T cell help (8). This model was based on the finding that IL-2 expressing tumor cells elicited systemic immunity in both the CT-26 colon carcinoma and B16 melanoma model, and that the tumor immunity depended only upon CD8+ cells. However, the inability to generate systemic immunity with IL-2 expressing B16 cells and the dependence of the GM-CSF effect upon CD4+ cells suggests that GM-CSF expressing cells may elicit systemic immunity in a fundamentally different manner.

Several characteristics of the immune response induced by vaccination with irradiated cells expressing GM-CSF suggest that the underlying mechanism may involve enhanced presentation of tumor-specific antigens by host antigen presenting cells. While the extent of systemic immunity induced by GM-CSF expressing cells was not appreciably affected by the level of GM-CSF secretion examined (FIG. 3B), the absolute number of vaccinating tumor cells was critical. This finding suggests that the absolute amount of tumor specific antigen available for vaccination may normally be limiting. Also, the injection of GM-CSF expressing cells led to a dramatic influx of monocytic cells, known to be potent antigen presenting cells (57), with lesser numbers of other cell types. Furthermore, both CD4+ and CD8+ cells were necessary for the immune response. Since the B16 cells used in this invention do not express detectable amounts of class II MHC molecules, even after γ-IFN treatment (unpublished results), it is likely that host antigen presenting cells, rather that the tumor cells themselves, were responsible for the priming of CD4+ T cells. These data are consistent with the hypothesis that local production of GM-CSF modifies the presentation of tumor antigens such that collaboration between CD4+ helper and CD8+ cytotoxic killer T cells is established or improved in vivo.

7.12. Use of Other Retroviral Vectors pLJ: The characteristics of this vector have been described in (20), and in U.S. Ser. No. 07/786,015, filed Oct. 31, 1991, and in PCT/US91/08121, filed Oct. 31, 1991. This vector is capable of expressing two types of genes: the gene of interest and dominant selectable marker gene, such as the neo gene. pLJ vectors containing murine IL-2, GM-CSF, IL-4, IL-5, γ-IFN, IL-6, ICAM, CD2 TNF-α, and IL1-RA (interleukin-1-receptor antagonist) are made. In addition, human sequences encoding TNF-α, GM-CSF and IL-2 are constructed. The gene of interest is cloned in direct orientation into a BamHI/SmaI/SalI cloning site just distal to the 5' LTR. The neo gene is placed distal to an internal promoter (from SV40) which is farther 3' than the cloning site (i.e. it is located 3' of the cloning site). Transcription from pLJ is initiated at two sites: the 5' LTR, which is responsible for the gene of interest, and the internal SV40 promoter, which is responsible for expression of the selectable marker gene. The structure pLJ is represented in FIG. 1B.

pEm: In this simple vector, described in U.S. Ser. No. 07/786,015, filed Oct. 31, 1991, abandoned, and in PCT/US91/08121, filed Oct. 31, 1991, the entire coding sequence for gag, pol, and env of the wild type virus is replaced with the gene of interest, which is the only gene expressed. The components of the pEm vector are described below. The 5' flanking sequence, 5' LTR and 400 base pairs of contiguous sequence (up to the BamHI site) are from pZIP. The 3' flanking sequence and LTR are also from PZIP; however, the ClaI site 150 base pairs upstream from the 3' LTR has been ligated with synthetic BamHI linkers and forms the other half of the BamHI cloning site present in the vector. The HindIII/EcoRI fragment of pBR322 forms the plasmid backbone. This vector is derived from sequences cloned from a strain of Moloney Murine Leukemia virus.

pEm vectors containing murine IL-2, GM-CSF, IL-4, IL-5, γT-IFN, IL-6, ICAM, CD2 TNF-α, and IL-1-RA (interleukin-1-receptor antagonist) are made. In addition, human sequences encoding TNF-α, GM-CSF and IL-2 are constructed.

αSGC: The α-SGC vector, described in U.S. Ser. No. 07/786,015, filed Oct. 31, 1991, abandoned and in PCT/US91/08121, filed Oct. 31, 1991, utilizes transcriptional promoter sequences from the α-globin gene to regulate expression of the cytokine-encoding gene. The 600 base pair fragment containing the promoter element additionally contains the sequences for the transcriptional initiation and 5' untranslated region of the authentic α-globin mRNA. A 360 base pair fragment which includes the transcriptional enhancer from cytomegalovirus precedes the α-globin promoter and is used to enhance transcription from this element. Additionally, the MMLV enhancer is deleted from the 3' LTR. This deletion is transferred to the 5' LTR upon infection and essentially inactivate the transcriptional activating activity of the element. The structure of α-SGC is represented in FIG. 1D.

α-SGC vectors containing murine IL-2, GM-CSF, IL-4, IL-5, γ-IFN, IL-6, ICAM, CD2 TNF-α, and IL-1-RA (interleukin-1-receptor antagonist) are made. In addition, human sequences encoding TNF-α, GM-CSF and IL-2 are constructed.

7.13. Co-administration of Viral Antigens and Cytokines

An appropriate vaccinating cell (which may include but not be restricted to, fibroblasts, keratinocytes, endothelial cells, monocytes, dentritic cells, B-cells or T-cells) would be infected with a retrovirus expressing an individual or combination of HIV antigens (including, but not limited to gag, env, Dol, rev, nef, tat, and vif), and a single or combination of cytokines (such as GM-CSF), irradiated or otherwise rendered proliferation incompetent, and administered to a patient.

7.14. Suppression of Immune Responses

An appropriate vaccinating cell (see example 13) as well as particular cells of an allograft (i.e. renal tubular epithelial cells in the kidney) would be infected with a virus expressing a single or combination of cytokines (such as gamma-interferon), irradiated or otherwise rendered proliferation incompetent, and administered to a patient to reduce the immune response against the allograft.

Additionally, the present invention can be used to suppress autoimmune diseases. The autoimmune response against a host target antigen could also be modified in a similar way. For example, the present invention could be used to treat multiple sclerosis. An appropriate cell (see example 13) would be infected with a retrovirus expressing myelin basic protein as well as a cytokine (such as gamma-interferon) to reduce the immune response directed against myelin basic protein in the patient.

7.15. Enhancement of Immune Response

It is also possible to use the present invention to enhance the immune response to a variety of infectious diseases. For example, the present invention could be utilized in the treatment of malaria. An appropriate vaccinating cell (see example 13) would be infected with a retrovirus expressing the gene form circumsporouzoite surface protein and a cytokine (such as GM-CSF), irradiated or otherwise rendered proliferation incompetent, and them administered to a patient to induce protection of a therapeutic response against malaria.

7.16. Human Clinical Studies

7.16.1. Melanoma Trials

Melanoma patients in which the disease had progressed to a stage where the surgery did not remain as an effective option were used in the study. The study also required that the patients show no evidence of autoimmune disease, serious allergy, or brain metastases (as determined by magnetic reasonance imaging, MRI), and retained adequate immune, hepatic, renal, and bone marrow function.

The huGM-CSF gene was subcloned into the insertion site of the retroviral vector MFG-S (a derivative of MFG) in a proper context and orientation for expression of the gene. The recombinant vector was subsequently transfected into the amphotropic packaging cell line pCRIP and high producer transfectants were isolated. High titer stocks of helper free retroviral particles which harbor the huGM-CSF gene were then harvested from the culture medium of the transfected packaging cell lines essentially as described above.

Tumor cells were resected from cutaneous and subcutaneous lesions, lymph nodes, and lung, liver, and soft tissue metastases. After resection, the specimens were aseptically transferred to a sterile container and transported to the laboratory. All subsequent procedures were conducted under aseptic conditions. The tumor tissues were disaggregated by either collagenase treatment or by mechanical dissociation and subsequently grown in culture and/or frozen in DMSO with 50 percent FCS (collagenase treated) or human albumin (mechanical dissociation). The numbers of the primary and secondary autologous tumor cells were expanded in culture, and a portion of the cells were subsequently transduced to produce huGM-CSF using an MFG-S construct.

After verification that the transduced cells were sterile, viable and producing cytokine, (see Table 2), a total of either $5\times10^6$ (low dose) or $5\times10^7$ (high dose) of the transduced tumor cells were irradiated, suspended in normal saline, and injected (both intradermally and subdermally at up to five different sites in volumes of 0.25–1.0 ml) back into the original donors. Up to three injections at the given dosages were applied to the individuals at approximately 21 day intervals. Control individuals were seperatively injected with irradiated non-transduced cells and levels of GM-CSF analogous to the amounts of GM-CSF produced by the transformed cells which were injected into the test subjects.

TABLE 2

GM-CSF Production (ng/$10^6$ cells/24 hrs)

| TEST SUBJECT | GM-CSF PRODUCTION |
|---|---|
| (Low Dose) | |
| 001 | 168.2 |
| 002 | 251.6 |
| 006 | 124.6 |
| 008 | 97.1 |
| 010 | 46.0 |
| 011 | 123.6 |
| 020 | 180.0 |
| (High Dose) | |
| 018 | 187.3 |
| 019 | 128.3 |

After injection, tests were performed to confirm that the transdcued tumor cells elicited an immune response. These tests included assaying for delayed type hypersensitivity (DTH) reactions to intradermally injected (irradiated) tumor cells, and biopsies of the vaccination and injection sites. The data indicate that T-cells are present in the inflamed tissues, and that there is a reporducible increase in the number of monocytes. The control subjects (who were injected with either nontransduced tumor cells or huGM-CSF at levels analogous to those produced by the transduced antologus tumor cells) showed little to none of the differences seen in the test subjects. Immunohistochemistry indicated that a tendency for antigenic drift correlated with decreased expression of the Mel 4 and HMB45 markers.

Additional tests were conducted to determine whether or not an increase in the number of eosinophils correlated with the injections. As seen in FIG. 10, after each vaccination, a transient increase in the percentage of eosinophils in the bloodstream generally followed.

The above data indicate that immune stimulation had occurred, and that the observed immune stimulation could be associated with the fact that the autologous tumor cells were expressing huGM-CSF in vivo.

7.16.2. Renal Cell Carcinoma Trials

Eighteen patients with advanced renal cell carcinoma were vaccinated up to four times (at approximately one month intervals) with either $4 \times 10^6$, $4 \times 10^7$, or $4 \times 10^8$ transduced and irradiated tumor cells. Tumor tissue was surgically resected (see above), and the population of primary and secondary tumor cells was expanded by in vitro culture. The cultured cells were subsequently transduced with the huGM-CSF/MFG-S construct described above, and tested for GM-CSF production. Transduced autologous cells which produced acceptable quantities of cytokine were irradiated and injected into the donor individuals as described above.

At the lowest dose of injected cells, the levels of GM-CSF secreted ranged between about 17 and 189 ng/$10^6$ cells/24 hrs. At the middle dose, the transduced cells constructed from the various individuals' tumors secreted between about 42 and 149 ng of GM-CSF/$10^6$ cells/24 hrs.

Control individuals were injected with irradiated non-transduced tumor cells. At the lowest dose, three subjects received non-transduced cells, at the middle dose of cells, five subjects received non-transduced cells, and the two patients that were injected with the highest dosage of cells only received nontransduced cells.

Patient responses to the vaccinations included marked erythema and induration at the injection site (Dose 1 showed the least response), which became more pronounced after multiple vaccinations (this was especially the case when transduced cells were injected).

Moreover, test subjects who were multiply injected with transduced cells also displayed positive DTH reactions, as well as an increase in the amount of eosiniphils (following vaccination). As in the melanoma study, apart from local symptoms (erythema, induration and itching), no significant adverse events were observed.

The above data reveal that the injection of irradiated autologous tumor cells expressing GM-CSF into human test subjects stimulated an observable in vivo tumor-specific immune response against the parent tumor cells.

It will be understood by those skilled in the art that various modifications of the present invention as described in the foregoing examples may be employed without departing from the scope of the invention. Many variations and modifications thereof will be apparent to those skilled in the art and can be made without departing from the spirit and scope of the invention herein described.

BIBLIOGRAPHY (1): Oettgen et al., The history of cancer immunotherapy. In Biologic Therapy of Cancer, Devita et al. eds. (J. Lippincott Co.) pp87–119 (1991)
(2): Asher et al., J. Immun. 146, 3227–3234 (1991)
(3): Havell et al., J. Exp. Med. 167, 1067–1085 (1988)
(4): Gansbacher et al., Cancer Res., 50, 7820–7825 (1990)
(5): Forni et al., Cancer and Met. Reviews, 7, 289–309 (1988)
(6): Watanabe et al., Proc. Natl. Acad. Sci. USA, 86, 9456–9460 (1989)
(7): Tepper et al., Cell, 57, 503–512 (1990)
(8): Fearon et al., Cell, 60, 397–403 (1990)
(9): Gansbacher et al., J. Exp. Med., 172, 1217–1224 (1990)
(10): Blankenstein et al., J. Exp. Med., 173, 1047–1052 (1991)
(11): Teng et al., Proc. Natl. Acad. Sci. USA, 88, 3535–3539 (1991)
(12): Colombo et al., J. Exp. Med., 173, 889–897 (1991)
(13): Rollins et al., Mol. Cell Bio., 11, 3125–3131 (1991)
(14): Hock et al., J. Exp. Med., 174, 1291–1298 (1991)
(15): Golumbek et al., Science, 254, 713–716 (1991)
(16): Foley, Cancer Res., 13, 835–837 (1953)
(17): Klein et al., Cancer Res., 20, 1561–1572 (1960)
(18): Prehn et al., J. Natl. Cancer Inst., 18, 769–778 (1957)
(19): Revesz, Cancer Res., 20, 443–451 (1960)
(20): Korman et al., Proc. Natl. Acad. Sci, USA, 84, 2150 (1987)
(21): Clerici et al., J. Immunol., 146, 2214–2219 (1991)
(22): Venet et al., J. Immunol., 148, 2899–2908 (1992)
(23): Hosmalin, et al. J. Immunol., 146, 1667–1673 (1991)
(24): Armentano et al., J. Virol., 61, 1647–1650 (1987)
(25): Sanger et al., Proc. Natl. Acad. Sci. USA, 74, 5463–5467 (1977)
(26): Yokota et al., Proc. Natl. Acad. Sci. USA, 82, 68–72 (1985)
(27): Lee et al., Proc. Natl. Acad. Sci. USA, 83, 2061–2065 (1986)
(28): Campbell et al., Europ. J. Biochem., 174, 345–352 (1988)
(29): Gough et al., EMBO J., 4, 645–653 (1985)
(30): Horley et al., EMBO J., 8, 2889–2896 (1989)
(31): Yagita et al., J. Immunol., 140, 1321–1326 (1988)
(32): Hamada et al., in preparation
(33): Wang et al., Science, 228, 149–154 (1985)
(34): Gearing et al., Production and assay of interleukin 2. In Lymphokines and Interferons: A Practical Approach. Clemens et al. eds. (IRL Press, Oxford, 1987) pp296–299.
(35): Hu-Li et al., J. Immunol., 142, 800–807 (1989)
(36): Le et al., Lymphokine Res. (US), 7, 99–106 (1988)
(37): Dexter et al., J. Exp. Med., 152, 1036–1047 (1980)
(38): Dugre et al.,Acta. Pathol. Microbiol. Immunol. Scand., 80, 863–870 (1972)
(39): Oliff et al., Cell, 50, 555–563 (1987)
(40): Hannum et al., Nature, 343, 336–340 (1990)
(41): Coligan et al., Current Protocols in Immunology (Greene Publishing Associates and Wiley-Interscience) 1991
(42): Takei, et al., J. Immunol., 134, 1403–1407 (1985)
(43): Danos et al. Proc. Natl. Acad. Sci. USA, 85, 6460 (1988)
(44): Parker et al., J. Virol., 31, 360–369 (1979)
(45): Southern, et al., J. Mol. Appl. Genet., 1, 327–341 (1982)
(46): Southern, J. Mol. Biol., 98, 503–517 (1975)
(47): Cone et al., Mol. Cell. Biol., 7, 887–897 (1987)
(48): Sambrook et al., Moleuclar Cloning: A Laboratory Manual (Cold Spring Harbor Press (1989)
(49): Feinberg et al., Anal. Biochem., 132, 6–13 (1983)
(50): Fidler et al., Cancer Res., 35, 218–234 (1975)
(51): Berd et al., J. Clim. Oncol., 8, 1858–1867 (1990)
(52): Rosenberg et al., N. Engl. J. Med., 319, 1676–1680 (1988)

(53): Brattain et al., *Cancer Res.,* 40, 2142–2146 (1980)
(54): Deleo et al., *J. Med. Exp.,* 146, 720–734 (1977)
(55): Murphy et al., *J. Natl. Cancer Inst.,* 50, 1013–1025 (1973)
(56): Bertram et al. *Cancer Letters,* 11, 63–73 (1980)
(57): Morrissey et al., *J. Immunol.,* 139, 1113–1119 (1987)

EQUIVALENTS

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. A method of stimulating a systemic immune response of a human to an established tumor, comprising administering to the human a therapeutically effective amount of tumor cells, wherein said tumor cells have been rendered proliferation incompetent by irradiation and have been genetically engineered to express granulocyte-macrophage colony stimulating factor, and wherein said tumor cells elicit a systemic immune response to said established tumor, and wherein said established tumor and said tumor cells are of the same type.

2. A method of stimulating a systemic immune response of a mammal to an established tumor comprising: administering tumor cells, wherein said tumor cells have been rendered proliferation incompetent by irradiation and have been genetically engineered to express granulocyte-macrophage colony stimulating factor, and wherein said tumor cells elicit a systemic immune response to said established tumor, and wherein said established tumor and said tumor cells are of the same type.

3. The method of claim 2 wherein said tumor cells further have been genetically engineered to express a protein selected from the group consisting of: IL-4, IL-6, CD2 and ICAM.

4. A method of suppressing growth of an established tumor in a mammal, comprising administering to said mammal: tumor cells wherein said tumor cells have been rendered proliferation incompetent by irradiation and have been genetically engineered to express granulocyte-macrophage colony stimulating factor and wherein said tumor cells elicit a systemic immune response to said established tumor such that growth of said established tumor is suppressed, and wherein said established or an said tumor cell are of the same type.

5. The method of any one of claims 2, 3, or 4, wherein said mammal is a human.

6. The method according to claim 5 wherein said granulocyte-macrophage colony stimulating factor is of human origin.

7. A method of suppressing growth of melanoma in a human comprising the step of administering to said human a therapeutically effective amount of proliferation-incompetent melanoma cells that have been genetically engineered to express granuloyte-macrophage colony stimulating factor, wherein said melanoma cells elicit a systemic immune response to said melanoma.

8. The method of claim 7, wherein said proliferation-incompetent melanoma cells are irradiated.

9. A method of suppressing growth of melanoma in a mammal comprising the step of administering to said mammal a therapeutically effective amount of proliferation-incompetent melanoma cells that have been genetically engineered to express granulocyte-macrophage colony stimulating factor, wherein said melanoma cells have been rendered proliferation incompetent by irradiation and wherein said melanoma cells elicit a systemic immune response to said melanoma.

* * * * *

UNITED STATES PATENT AND TRADEMARK OFFICE
CERTIFICATE OF CORRECTION

PATENT NO : 5,904,920
DATED : May 18, 1999
INVENTOR(S): Dranoff et al.

It is certified that error appears in the above-identified patent and that said Letters Patent is hereby corrected as shown below:

```
In claim 1, line 16, after "to", "the" should be changed to --said--.
In claim 2, line 24, "tumor" should be changed to --tumor,--.
In claim 2, line 24, "comprising:" should be changed to --comprising--.
In claim 2, line 30, after "response", insert --specific--.
In claim 4, line 3, "mammal:" should be changed to --mammal--.
In claim 4, line 3, "cells" should be changed to --cells,--.
In claim 6, line 13, after "method", "according to" should be
changed to --of--.
In claim 7, line 17, "human" should be changed to --human,--.
In claim 7, line 17, after "comprising", delete "the step of".
In claim 9, line 26, "mammal" should be changed to --mammal,--.
In claim 9, line 26, after "comprising", delete "the step of".
```

Signed and Sealed this

Twenty-eighth Day of December, 1999

*Attest:*

Q. TODD DICKINSON

*Attesting Officer*   *Acting Commissioner of Patents and Trademarks*